United States Patent [19]

Ferrari et al.

[11] Patent Number: 5,243,038

[45] Date of Patent: Sep. 7, 1993

[54] CONSTRUCTION OF SYNTHETIC DNA AND ITS USE IN LARGE POLYPEPTIDE SYNTHESIS

[75] Inventors: Franco A. Ferrari, La Jolla; Charles Richardson; James Chambers, both of San Diego; Stuart C. Causey, Del Mar; Thomas J. Pollock, San Diego; Joseph Capello, San Diego; John W. Crissman, San Diego, all of Calif.

[73] Assignee: Protein Polymer Technologies, Inc., San Diego, Calif.

[21] Appl. No.: 114,618

[22] Filed: Oct. 29, 1987
(Under 37 CFR 1.47)

Related U.S. Application Data

[63] Continuation-in-part of Ser. No. 927,258, Nov. 4, 1986, abandoned.

[51] Int. Cl.$^5$ .................... C12N 15/11; C12N 15/62; C07K 13/00
[52] U.S. Cl. .................... 536/23.1; 536/23.4; 435/69.1; 435/320.1; 435/172.3; 530/353; 935/10; 935/60
[58] Field of Search .......... 435/320, 68, 172.3, 435/91, 252.3, 69.1, 320.1; 350/353; 536/27, 22.1, 23.1, 23.4; 935/10, 60

[56] References Cited

U.S. PATENT DOCUMENTS

| | | | |
|---|---|---|---|
| 4,132,746 | 1/1979 | Urry et al. | 525/432 |
| 4,187,852 | 2/1980 | Urry et al. | 600/36 |
| 4,474,851 | 10/1984 | Urry | 428/373 |
| 4,500,700 | 2/1985 | Urry | 528/328 |
| 4,589,882 | 5/1986 | Urry | 623/11 |
| 5,149,657 | 9/1992 | Maugh et al. | 435/69.1 |

FOREIGN PATENT DOCUMENTS 2162190A 1/1986 United Kingdom .

OTHER PUBLICATIONS

Kempe, et al. *Gene* 39:239–245, 1985.
Nakajima, et al. *Chem. Abs* 93:95638, 1980.
Bressan, G. M. et al. 1987. *Biochemistry* vol. 26 pp. 1497–1503.
Shen, S-H. 1984. *Proc. Nat. Acad. Sci. USA* vol. 81 pp. 4627–4631.
Doel, M. T. et al. 1980. *Nucleic Acids Res.* vol. 8, pp. 4575–4592.
Hartley, J. L. et al. 1981. *Gene* vol. 13, pp. 347–353.
Gage, L. P. et al. 1980. *J. Biol. Chem.* vol. 255, pp. 9444–9450.
Gupta, S. C. et al. 1983. *Bio/Technology* vol. 1 pp. 602–609.
Sadler, J. R. et al. 1980. *Gene* vol. 8, pp. 279–300.
Jarman, T. et al. 1985. *World Biotech Rep.*, vol. 1 pp. 505–512.
Dixon, B. 1985. *Bio/Technology* vol. 3 p. 671.
Lotz, B. et al. 1982, *J. Mol. Biol.* vol. 156 pp. 345–357.
Allbertini, A. M. et al. 1982. *Cell* vol. 29 pp. 319–328.
Bell, J. R. et al. 1974, *Int. J. Peptide Protein Res*, vol. 6 pp. 155–156.
Urry, "Protein Elasticity of Sequential Polypeptides," *J. Prot. Chem.* (1984) 3:403–436.
Foster et al., "Isolation and Amino Acid Sequences of Tropoelastin Peptides," *J. Biol. Chem.* (1979) 248:2876–2879.
Sandberg et al., "Elastin structure, biosynthesis and relation to disease states," *N. Engl. J. Med.* (1981) 304:566–579.

Primary Examiner—Richard A. Schwartz
Assistant Examiner—Mary E. Mosher
Attorney, Agent, or Firm—Bertram I. Rowland

[57] ABSTRACT

Methods are provided for the production of large polypeptides containing repeating sequences of amino acids utilizing biochemical techniques, specifically DNA sequences coding for the expression of the large polypeptides. Systems utilizing exogenous transcriptional and translational regions to control the production of the large polypeptides are also provided.

7 Claims, 10 Drawing Sheets

```
                                                        ┌─β-lactamase
m  t  m  i  t  p  s  l  g  c  r  s  t  l  e  d  p  h  f  r
ATGACCATGATTACGCCAAGCTTGGGCTGCAGGTCGACTCTAGAGGATCCCCATTTCCGT
              HindIII PstI SalI XbaI BamHI
                                           -1 +1 of mature β-lactamase
v  a  l  i  p  f  f  a  a  f  c  l  p  v  p  a  h
GTCGCCCTTATTCCCTTTTTTGCGGCATTTTGCCTTCCTGTTTTTGCTCAC...
```

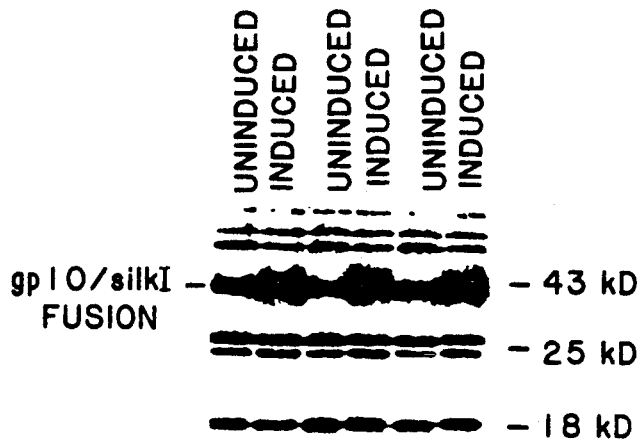
FIG.4A
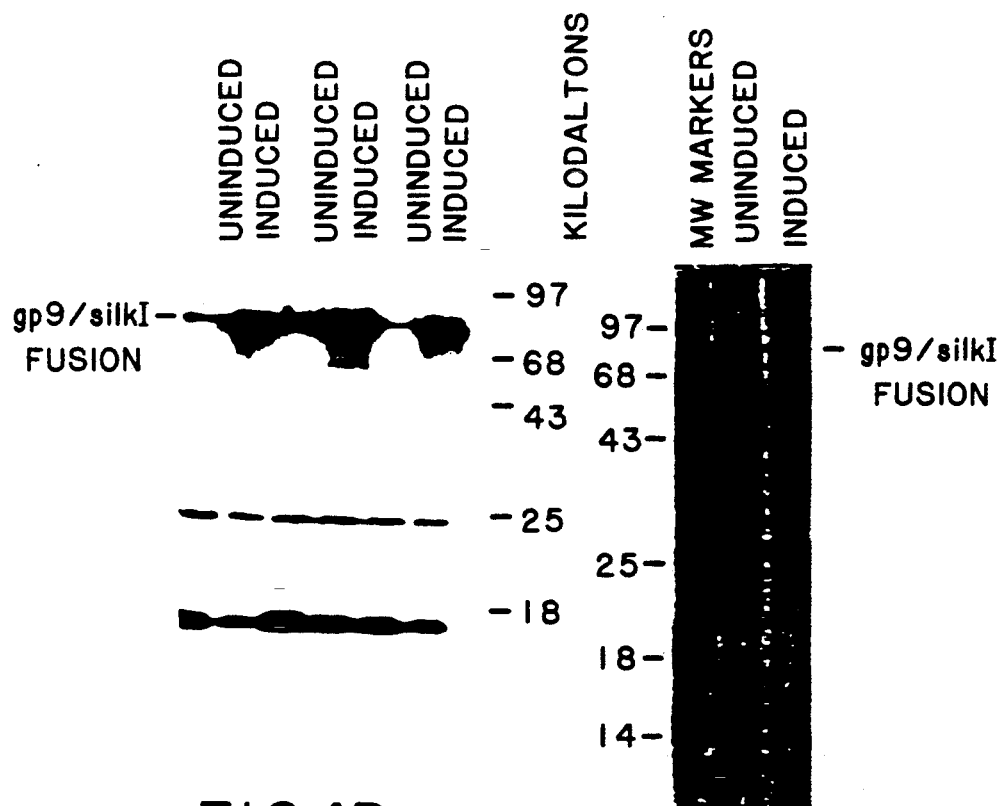
FIG.4B
FIG.4C

CONSTRUCTION OF SYNTHETIC DNA AND ITS USE IN LARGE POLYPEPTIDE SYNTHESIS

The government has certain rights in this invention as a result of support provided by the Department of the Navy for the work leading to the present invention.

CROSS-REFERENCE TO RELATED APPLICATIONS

This application is a continuation-in-part of application Ser. No. 927,258, filed Nov. 4, 1986, now abandoned.

INTRODUCTION

2. Technical Field

The field is related to the production of high-molecular-weight polymers, either nucleic acids or peptides that are the expression products of the nucleic acids, and is particularly related to the production of high-molecular-weight peptides containing repeating sequences by biochemical processes, the peptide finding use as structured materials.

2. Background

Recombinant DNA technology has been applied in the isolation of natural genes and the expression of these genes in a variety of host cells. Typically, this technology has had utility in producing biologically active polypeptides, such as interferons or peptide hormones, which were impractical to produce in useful amounts by other means. It was also possible to produce modified proteins by isolating natural genes and utilizing the techniques of site specific, in vitro mutagenesis to alter these genes and thereby change the polypeptides produced. Other polypeptides have been created by combining sections of various native genes to produce new polypeptides that are chimeric molecules of the several naturally occurring molecules.

With the advent of efficient and automated methods for the chemical synthesis of DNA, it has become possible to synthesize entire genes and to modify such synthetic genes at will during the course of synthesis. However, these various technologies have been applied to the production of natural or modified versions of natural polypeptides. There have been very few attempts to use these technologies to create substantially new polypeptides. In nature, polypeptides have a wide range of chemical, physical and physiological characteristics. Nevertheless there are commercial applications for which known, naturally occurring polypeptides are not appropriate.

While biotechnology is versatile, usually it has been limited in its applications of naturally occurring products or modifications of naturally occurring molecules. One great strength of organic chemical synthesis, by contrast, has been the ability to transform inexpensive carbon materials to a wide variety of polymeric molecules, including naturally occurring molecules, but most importantly entirely new chemical structures, such as polypropylene and polyacrylates, which have defined and predicted chemical properties not associated with naturally occurring molecules.

Such materials, particularly high-molecular-weight polymers containing repeating sequences of amino acids, have proven difficult to produce by biochemical means. The genes necessary for producing large peptides containing repeating units of amino acids were unstable and often underwent intermolecular recombination causing deletions of repeating units in the gene. The development of a biotechnology which would produce polymeric molecules by biological processes similar to those available by organic synthesis would significantly broaden the range of applications of biotechnology.

BRIEF DESCRIPTION OF THE RELEVANT LITERATURE

The cloning of multiple lactose operators up to four in tandem is disclosed by Sadler et al., *Gene*, (1980) 8:279–300. Hybrid bacterial plasmids containing highly repeated satellite DNA is disclosed by Brutlag et al., *Cell*, (1977) 10:509–519. The synthesis of a poly(aspartyl-phenylalanine) in bacteria is disclosed by Doel et al., *Nucleic Acids Research*, (1980) 8:4575–4592. A method for enriching for proline content by cloning a plasmid which codes for the production of a proline polymer was disclosed by Kangas et al., *Applied and Environmental Microbiology*, (1982) 43:629–635. The biological limitations on the length of highly repetitive DNA sequences that may be stably maintained within plasmid replicons is discussed by Gupta et al. in Bio/Technology, p. 602–609, September 1983.

SUMMARY OF THE INVENTION

Methods and compositions are provided for the production of polypeptides having repetitive oligomeric units by expression of a synthetic structural gene. The individual units coding for an oligomeric peptide sequence are varied as to nucleotide sequence utilizing amino acid codon redundancy. Long nucleic acid sequences are built up by synthesizing nucleic acid oligomers which express a plurality of individual repetitive peptide units, and the oligomers are joined to provide a polynucleotide of the desired length. Expression systems are used which provide for the growth of the subject host to high density prior to significant expression of the polypeptide product, followed by induction of expression to provide high yields of the polypeptides produce, which can be isolated from the host cells. In one embodiment, a system is employed where the transcription initiation system of the synthetic gene is not recognized by the host RNA polymerase and a gene expressing a functional RNA polymerase under inducible regulation is included in the host.

BRIEF DESCRIPTION OF THE FIGURES

FIG. 4A–B: Immunoblots of polypeptide products (A) T7gp10/SlpI with anti-Slp Ab, (B) T7gp9/SlpI with anti-Slp Ab, or (C) staining with Coomassie blue.

DESCRIPTION OF PREFERRED EMBODIMENTS

Figure 1:
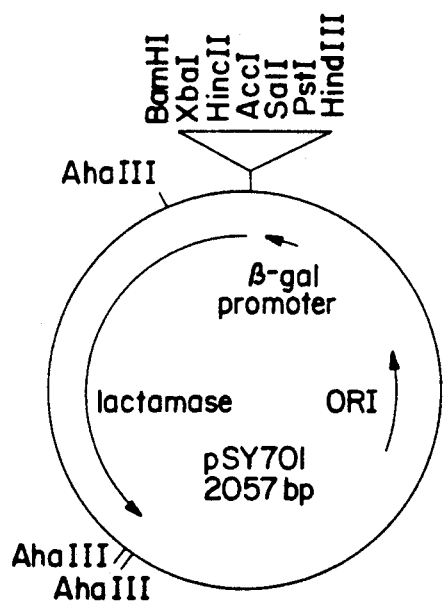
FIG. 1: Plasmid pSY701 structure.

Novel polypeptides are provided which are polyoligomers or repeating, relatively short, amino acid sequence units. The oligomers may be linked by spacers of different amino acid sequence. The novel polypeptides therefore contain repetitive amino acid sequences and are particularly useful as fibrous proteins, including elastomeric. The gene encoding the repeating-unit-containing peptides is produced to particularly avoid problems previously associated with genes containing multiple repeating units.

The genes of the subject invention comprise multimers of DNA sequences encoding the same amino acid sequence unit, where two or more different multimers encoding different amino acid units may be joined together to form a block copolymer. The individual units will have from 4 to 30 amino acids (12 to 120 nt), more usually 4 to 25 amino acids (12 to 75 nt), particularly 4 to 8 amino acids, usually having the same amino acid appear at least twice in the same unit, generally separated by at least one amino acid. The units of the multimer coding for the same amino acid sequence may involve two or more nucleotide sequences, relying on the codon redundancy to achieve the same amino acid sequence.

For the most part the DNA compositions of this invention may be depicted by the following formula:

$$K_k(W\ M\ X_x\ N\ Y_y)_i\ L_l$$

wherein:

K is a DNA sequence encoding an amino acid sequence of from about 1 to 100 amino acids, usually 1 to 60 amino acids, which may be any sequence, generally being fewer than about 20% of the total number of amino acids, more generally being fewer than about 10% of the total number of amino acids, which may be any sequence, particularly a naturally occurring sequence where the multimer structural gene has been fused to another DNA sequence in reading frame. K will have the initiation methionine codon.

k is 0 or 1;

W has the formula:

$$[(A)_n(B)_p]_q$$

wherein:

A is a DNA sequence coding each time that it appears for the same amino acid sequence unit normally having at least one amino acid appear at least twice in the sequence, where A will generally be from about 12 to 90 nucleotides (nt), more usually for about 12 to 75 nucleotides.

where there will usually be at least two different A's, usually not more than ten different A's, more usually not more than six different A's, which code for the same amino acid sequence but differ from each other by at least one nucleotide and may differ by as many as ten nucleotides, usually not differing by more than about five nucleotides from another A sequence, each of the different A's usually being repeated at least twice; at least two different codons are employed for the same amino acid, e.g., GGC and GGA for glycine, in different A's coding for the same amino acid sequence unit;

n will be an integer of at least 2, usually at least about 8, and not more than about 250, usually not more than about 200, frequently not more than about 125, and in some instances may not exceed about 50;

B is a DNA sequence different from A coding for an amino acid sequence other than the amino acid sequence unit coded by the A unit and serves as a linking unit between oligomers of A units. B will generally have from about 3 to 45 nt, (1 to 15 amino acids) more usually from about 3 to 30 nt (1 to 10 amino acids);

where the B units appearing in the gene may be the same or different, there usually not being more than about 10 different B units, more usually not more than about 5 different B units, where the B units may differ in from 1 to 45 nt, more usually from about 1 to 15 nt, where the different B's may code for the same or different amino acid sequencer;

p is 0 or 1 and may differ each time there is a successive A unit;

q is an integer of at least 1 and will vary with the number of nucleotides in A and B, as well as the values of n and p. The variable q will be selected so as to provide for at least 90 nucleotides for the multimeric portion of the structural gene, preferably at least about 150 nt, more preferably at least 450 nt, and most preferably at least 900 nucleotides, and the number of nucleotides will usually not exceed about 10,000, more usually not exceeding about 8,000, generally being in the range of about 900 to 6,000, more usually to about 5,000; and M is a DNA nucleotide sequence of 0 to 18 nt, which may encode any amino acid sequence, usually including amino acids of A and/or B, generally limited to the amino acids of A and/or B;

X may be the same as or different from W, usually different, and will have the formula $$[(A^1)_{n1}\ (B^1)_{p1}]_{q1}$$

wherein:

$A^1$, $B^1$, $N^1$, $p^1$ and $q^1$ are the same as or different from A, B, n, p and q respectively, at least one being different, wherein the analogous symbols come within the same definition as their counterparts;

x is 0 or 1;

N is the same as or different from M and comes within the same definition as M;

Y may be the same as or different from W, usually different, and will have the formula $$[A^2)_{n2}(B^2)_{p2}]_{q2}$$

wherein:

$A^1$, $B^2$, $n^2$, $p^2$ and $q^2$ are the same as or different from A, B, n, p and q respectively, at least one being different, wherein the analogous symbols come within the same definitions as their counterparts.

y is 0 or 1;

i is 1 to 100, usually 1 to 50, more usually 1 to 30, particularly 1, when x and y are 0;

when x or y are 1, q, $q^1$ and $q^2$ will be a total of at least 2, usually at least 5 and not more than about 50, usually not more than about 30.

The total number of nucleotides will be at least 90 nucleotides, usually at least about 150 nt, preferably at least about 900 nt and may be 20 knt (kilonucleotides), usually not more than about 15 nt, more usually not more than about 10 knt.

The polypeptide encoded by the above DNA sequence will have the following formula:

$$K'_k(W'M'X'_xN'Y'_y)_iL'_l$$

wherein:
W' will have the following formula $$[(D)_n(E)_p]_q$$

wherein:
D is the amino acid sequence encoded for by A and therefore has the numerical limitations based on 3 nucleotides defining a codon that codes for one amino acid;

E is the amino acid sequence encoded for by B, and therefore has the numerical limitations based on 3 nucleotides defining a codon, where each E may be the same or different, depending upon the coding of B;

and, wherein, likewise K', W', M', X', N', Y' and L' is the amino acid sequence encoded for by K, W, M, X, N, Y and L respectively. However, in the case of K and L, subsequent processing, such as protease treatment, cyanogen bromide treatment, etc. may result in partial or complete removal of the N- or C-terminal non-multimeric chains.

n, p, q, k, i and l have the same definitions as previously indicated.

Particular polymeric compositions having repeating multimeric units having the same compositions (A) will have the following formula where x and y are 0, $$K'_k[(D)_n(E)_p]_qL'_l$$

where
all of the symbols have been defined previously; and the DNA sequence will have the formula $$K_k[(A)_n(B)_p]_qL_l$$

where
all of the symbols have been defined previously.

Particular DNA sequences encoding copolymeric compositions having a repeating unit of two to three multimeric blocks will have the following formula:

$$K_k(W''M''X''N''Y''_y)_{i'}L_l$$

wherein:
W'' is a multimer having the formula $$[(A^3)_{n3}(B^3)_{p3}]_{q3},$$

where
$A^3$ is of 4 to 8, usually 4 to 6 codons, otherwise coming within the definition of A;
$n^3$ will be from about 2 to 12, usually 2 to 10;
$B^3$ is of from 2 to 8, usually 4 to 6 codons;
$p^3$ is 0 or 1;
$q^3$ is of from about 2 to 25, usually 2 to 20;
X'' and Y'' are the same as or different from W'', usually different, coming within the same definitions as W'';
M'' and N'' come within the definitions of M' and N';
i'' is at least 2, usually at least 5 and not more than about 75, usually not more than about 50, generally not exceeding 30;
with the other symbols as defined previously.

The compositions of the invention will usually have a molecular weight of at least about 5 kDal, usually 10 kDal, preferably 15 kDal and may have molecular weights as high or higher as 400 kDal, usually not exceeding 300 kDal, more usually not exceeding about 250 kDal, the higher ranges generally being the multimer combinations, with the individual multimer usually being less than about 150 kDal, usually less than about 100 kDal.

The nucleotide sequences which are employed will be synthesized, so that the repetitive units will have different codons for the same amino acid as described above. Usually, at least about 25%, more usually at least about 40%, and generally at least about 60%, but not greater than about 95%, preferably not greater than about 90% of the nucleotide sequences encoding the repetitive units will be the same. Greater diversity within those ranges will be employed where the initial constructs are experimentally shown to undergo spontaneous recombination events.

Of particular interest are polypeptides which has as a repeating unit SGAGAG (G=glycine; A=alanine; S=serine). This repeating unit is found in a naturally occurring silk fibroin protein, which can be represented as GAGAG(SGAGAG)$_8$SGAAGY (Y=tyrosine). In the subject invention, the repeating unit is designed where the N-terminus may be MGAGAG or any other sequence of generally at least about 3 amino acids, usually at least about 5 amino acids, more usually 12 amino acids and not greater than 200, usually not greater than 100 amino acids, which may be different from the repetitive unit. Generally, a different N-terminus will be the result of insertion of the gene into a vector in a manner that results in expression of a fusion protein. Any protein which does not interfere with the desired properties of the product may provide the N-terminus. Particularly, endogenous host proteins, e.g. bacterial proteins, may be employed. The choice of protein may depend on the nature of the transcriptional initiation region. Similarly, the C-terminus may have an amino acid sequence different from the repeat sequence. Conveniently, there may be from 1 to 100, usually 1 to 25 amino acids, which may be the C-terminus of a naturally occurring structural gene, which again typically results from the formation of a fusion product.

A silk-like-protein (Slp) gene may be produced by providing oligomers of from about 5 to 25 repeat units as described above, more usually of about 10 to 20 repeat units. By having different cohesive ends, the oligomers may be concatemerized to provide for the polymer having 2 or more of the oligomeric units, usually not more than about 50 oligomeric units, more usually not more than about 30 oligomeric units, and frequently not more than about 25 oligomeric units.

The silk-like proteins may be varied by having alternate multimers with the same or different handedness. For example, in the formula, $(B)_p$ may provide an even or odd number of amino acids. In silk, the hydrogens of the glycine may align on one side and the methyls and hydroxyls of alanine and serine on the other. If $(B)_p$ is even, there will be continuous alignment, if odd, there will be alternating alignment of $(A)_n$. Thus, different properties can be achieved by changing the number of amino acids encoded by $(B)_p$.

Of particular interest are polypeptides which mimic the composition and physical properties of silk of *Bombyx mori.*

Also of interest are polypeptides which have as a base repeating unit GVGVP (G=glycine, V=valine, P=proline), which may be found in naturally occurring elastin. In the subject invention, the N-terminus may be any convenient sequence and, if desired, may be in whole or in part removed by a protease. Usually the N-terminal sequence which does not have the subject motif will be less than about 100 amino acids, more usually less than about 60 amino acids.

Of particular interest is a base sequence of about 6 to 10, preferably 8, units separated by a sequence of about 6 to 20 amino acids, usually 8 to 16 amino acids, which may include an internal repeat different from the basic repeating unit of from 4 to 8 amino acids. For example, the second repeat sequence could be GAGAGS, repeated twice. The total number of base repeating units will generally be in the range of about 150 to 300, usually 175 to 250. The C-terminus may terminate with a repetitive unit or portion thereof or a different sequence of from 1 to 100, usually 1 to 30 amino acids. The C-terminus is not critical to the invention and will be selected primarily for convenience. As with the N-terminus, it may be designed for proteolytic cleavage. As in the case of the silk protein, the subject elastin-like protein may be similarly engineered.

Of particular interest are proteins which mimic the properties of elastin and provide for elastomeric properties.

The copolymer involving repeating units is a powerful method for varying properties, by appropriate choice of the different units, the number of units in each multimer, the spacing between them, and the number of repeats of the multimer combination assembly. Thus, by varying the number and arrangement of primary monomers, a variety of different physical and chemical properties can be achieved.

Exemplary of the use of the block copolymers are combinations of silk units and elastin units to provide products having properties distinctive form polymers only having the same monomeric unit.

To prepare the structural genes, various approaches can be employed. To prepare the oligomers, complementary strands of DNA may be synthesized, so that upon hybridization double-stranded DNA is obtained with the appropriate termini. If desired, each of the oligomeric units may be the same, so that in a single step, a concatemer may be obtained depending upon the conditions of the hybridization. Normally, conventional annealing and ligating conditions will be employed, such as are described in the examples that follow.

If desired, two different oligomeric units may be prepared where the termini of the two units are complementary one with the other but the termini of the same unit are unable to bind together. In this way one can build individual oligomeric units and then join them together to form the concatemer, where the intervening linking sequences are defined at least in part by the termini. Depending upon the construct, the 5' terminus may provide for the initiation codon methionine, or the structural gene may be joined to an adapter which may provide for a unique sequence (optionally cleavable by a specific enzyme) at the 5' terminus or may be inserted into a portion of gene, usually endogenous to the host, in proper reading frame so as to provide for a fusion product. By providing for appropriate complementary termini between the adapter or truncated gene and the 5' end of the subject structural gene, the sequences can be joined in proper reading frame to provide for the desired protein. Advantages that may be achieved by employing adapters or fusion proteins include having specific sequences for special purposes, such as linking, secretion, complex formation with other proteins, affinity purification, or the like.

Once the structural gene has been assembled, it may be cloned; clones having the desired gene, particularly as to sequence length, may be isolated; and the gene may be removed and used to join to a sequence for expression.

The expression construct will include transcriptional and translational initiation and termination regulatory regions, 5' and 3', respectively, of the structural gene. As already indicated, these regions may be created by employing a fusion protein, where the subject structural gene is inserted into a different structural gene downstream from its initiation codon and in reading frame with the initiation codon. Alternatively, various transcriptional and translational initiation regions are available from a wide variety of genes for use in expression hosts, so that these transcriptional and translational initiation regions may be joined to the subject structural gene to provide for transcription and translation initiation of the subject structural genes. A wide variety of termination regions are available which may be from the same gene as the transcriptional initiation region or from a different gene. Numerous constructs have been disclosed in the literature, and the same procedures may be applied with the subject gene as have been employed with other structural genes.

Of particular interest is the use of an inducible transcription initiation region. In this manner, the host strain may be grown to high density prior to significant expression of the desired product. Providing for inducible transcription is particularly useful where the peptide is retained in the cellular host rather than secreted by the host.

A number of inducible transcription initiation regions exist or can be employed in particular situations. The inducible regions may be controlled by a particular chemical, such as isopropyl thiogalactoside (IPTG) for inducing the beta-galactosidase gene. Other inducible regions include lambda left and right promoters; various amino acid polycistrons, e.g., histidine and tryptophan; temperature sensitive promoters; and regulatory genes, e.g., $cI^{ts}857$.

An alternative system which may be employed with advantage is use of a combination of transcription initiation regions. A first transcription initiation region which regulates the expression of the desired gene but which is not functional in the expression host by failing to be functional with the endogenous RNA polymerase is employed. A second transcription initiation region, such as an inducible region, can then be employed to regulate the expression of an RNA polymerase with which the first transcription initiation region is functional. In this manner expression only occurs upon activation of the regulatory region controlling the expression of the exogenous RNA polymerase. In the subject application, this system is illustrated with the T7 phage transcription initiation region, specifically the initiation regions are genes 9 and 10 of T7 phage.

An alternative system relies on the use of mutants which undergo a developmental change based on a change in the environment, such as a lack of a nutrient, temperature, osmotic pressure, salinity, or the like. Illustrative of this system, strains of B. subtilis can be obtained which are incapable of sporulation but which can produce those components which initiate expression of products involved with sporulation. Therefore, by a change in the condition of the medium, a transcription initiation region associated with sporulation will be activated. In this situation, the host provides the necessary inducing agent or activator to initiate expression.

Various other techniques exist for providing for inducible regulation of transcriptional and translation of a gene in a particular host.

For the most part, the host will be a unicellular organism, either a prokaryote or a eukaryote, selected from bacteria, algae, fungi, filamentous fungi, etc. Illustrative hosts include *E. coli, B. subtilis, B. stearothermophilus, S. cerevisiae,* and the like.

The expression construct for expression of the desired gene, by itself or in conjunction with any auxiliary genes involved with transcription, will normally be joined in an appropriate vector for introduction into the expression host. A large number of vectors are commercially available with others being described in the literature. The vectors are normally characterized by having one or more unique restriction sites, a replication system for extrachromosomal maintenance in the host, and one or more markers which allow for selective pressure on the host. The markers may provide complementation, prototrophy to an auxotrophic host, resistance to a biocide, e.g., an antibiotic such as penicillin or kanamycin, or the like. In some instances, rather than selective pressure, a marker gene is employed which allows for detection of particular colonies containing the gene. This situation is illustrated by the gene for beta-galactosidase, where a substrate is employed which provides for a colored product.

The expression construct, including any auxiliary genes, may be introduced into the expression vector in accordance with known techniques, particularly employing restriction, insertion, and ligation.

The expression construct may then be used for transformation of the appropriate host. Depending upon the host, either intact cells or protoplast may be employed, where transformation or conjugation is employed. Conveniently, calcium-phosphate-precipitated DNA or non-ionic detergents may be employed to introduce the plasmid into the host. It should be appreciated that it is not necessary to employ vectors for host transformation, since bare DNA can be introduced for integration into the genome. However, even where integration is desired, a much greater efficiency of integration is achieved employing the vectors, thus favoring the employment of vectors.

Depending upon the nature of the vector, the expression construct may be maintained on an extrachromosomal element or become integrated into the host. Where integration is desired, it will usually be desirable with prokaryotes and some eukaryotes to have a sequence homologous to a sequence in the chromosome of the host. Usually the sequence will be at least about 200 bp and not more than about 5000 bp, usually not more than about 2000 bp. The choice of the homologous sequence is somewhat arbitrary, but may be used for complementation, where the host is an auxotrophic mutant and the homology provides prototrophy.

The transformants or integrants may then be grown in an appropriate nutrient medium to high density, followed by induction of transcription in accordance with the nature of the transcriptional system of the expression construct. Where the desired protein is retained in the cytoplasm, these cells are harvested and lysed, and, depending upon the use of the protein, the protein may be further purified in accordance with conventional techniques, such as chromatography, solvent-solvent extraction, affinity chromatography, and the like.

The repetitive proteins can find a variety of uses. The Slp proteins may be used in producing fibers having unique properties, as a substitute for silk, and the like. Collagen proteins can be produced, where the collagen is free of the telopeptide or contains the telopeptide, depending upon its functions. Atelopeptidecollagen should have little if any immunogenicity, so as to be a useful structural element for a variety of prosthetic devices or for use as a collagen substitute in other applications. Similarly, other proteins having repetitive sequences, such as keratin, can also be prepared in accordance with the subject invention. Other useful repetitive proteins can be prepared based on sequences of spider silks and other repetitive animal fibers. Artificial peptides useful for immunization could also be prepared based on repeating sequences present in various surface antigens of disease-causing microorganisms, such as parasites, bacteria, and viruses.

The following examples are offered by of illustration and not with limitation.

EXAMPLE 1

DNA Preparation Methods

1. Preparation of plasmid DNA from *E. coli*

A. Small scale: Plasmid DNA was prepared from 1.5 ml cultures by either the boiling procedure or the alkaline lysis method (Maniatis, et al., Molecular Cloning: A Laboratory Manual. Cold Spring Harbor Laboratory, Cold Spring Harbor. (1982)).

B. Large scale: A plasmid-carrying strain was grown overnight in 1 liter of Luria broth with the appropriate antibiotic. The cells were collected by centrifugation at 10,000 xg for 5 min and resuspended in 10 ml of ice cold TE (10 mM Tris-HCl pH 8, 1 mM EDTA). The cells were centrifuged again, resuspended in 4 ml of TES (TE and 25% w/v sucrose) and homogenized by vortexing. The samples were kept on ice for the following steps. Lysozyme (1 ml of 10 mg/ml) was added to the cell suspension and incubated for 5 min before the addition of 2 ml of 0.5M EDTA pH 8. After 10 min incubation, 50 ml of proteinase K (40 mg/ml) were added followed 10 min later with 15 ml of lysing buffer (0.1% triton X-100, 1 mM EDTA, 50 mM tris-HCl pH 8). After 15-20 min, the cell lysate was centrifuged at 35,000 xg for 90-120 min. The supernatant (19.8 ml) was transferred to a plastic tube with 20 g of CaCl and 400 $\mu$l of ethidium bromide (10 mg/ml). After dissolution, the mixture was divided into two polyallomer ultracentrifuge tubes, sealed with heat and centrifuged in a Beckman Ti 65 motor at 60,000 rpm for 24 hr. The lower plasmid DNA band was removed from the tube with a hypodermic needle. The ethidium bromide was extracted three times with an equal volume of NaCl-saturated isopropanol. Two volumes of $H_2O$ were added to the DNA solution, and then the DNA was precipitated with ethanol.

2. Preparation of double-stranded DNA

A culture of JM103 was grown to an $OD_{600}$ of about 0.2 and then divided into aliquots of 2 ml. Each aliquot was infected with a fresh plaque of M13 and incubated at 37° C. for about 6 hr with vigorous shaking. Then the cells were pelleted and the supernatant was saved for subsequent infections. The double-stranded phage DNA was extracted by the boiling method (Maniatis et al.).

3. Deproteinization

Phenol extraction was performed on a convenient volume of DNA sample, typically between 100 μl to 10 ml. The DNA sample was diluted in 0.01M Tris-HCl pH 7.5, 1 mM EDTA and an equal volume of water-saturated phenol was added. The sample was vortexed briefly and placed on ice for 3 min. After centrifugation for 3 min in a microfuge, the aqueous layer was removed to a new tube and extracted once with an equal volume of chloroform:isoamylalcohol (24:1).

4. Ethanol precipitation

DNA in a aqueous buffer was concentrated by ethanol precipitation. To the DNA sample was added 1/10 volume of 3M sodium acetate pH 7.5 and 2-3 volumes of cold ethanol. The DNA was precipitated for 30 min at $-70°$ C. or overnight at $-20°$ C. and then pelleted by centrifugation in the microfuge for 15 min at 4° C. The pellet was washed once with 200 μl of cold 80% ethanol and pelleted again for 10 min at 4° C. After air drying or lyophilization, the pellets were resuspended in the appropriate buffer.

5. Phosphatase treatment of DNA

Phosphatase treatment of DNA was performed by adding 1 μl (25 units) of calf intestinal phosphatase (Boeringer Mannheim) directly to the restriction enzyme digestion reaction and continuing the incubation for 30 min at 37° C. The phosphatase was inactivated for 60 min at 65° C. prior to deproteinization by phenol extraction.

6. Fill-in reaction with DNA polymerase I

DNA was resuspended in buffer containing 50 mM Tris-HCl pH 7.4, 50 mM KCl, 5 mM $MgCl_2$, and 400 μM each of the four deoxynucleotide triphosphate. Ten units of Klenow DNA polymerase (BRL) were added, and the reaction was allowed to proceed for 15 min at room temperature. The DNA was then phenol extracted and ethanol precipitated.

7. T4 polynucleotide kinase reaction

The reaction (10 μl) contained: T4 polynucleotide kinase (BRL), 150 ng of DNA, 1 μl of 10 x kinase buffer (0.7M Tris-HCl pH 7.6, 0.1M $MgCl_2$, 50 mM DTT) and [$^{32}P$]-ATP (200-300 nCi). This was incubated at 37° C. for 30 min and then the DNA was purified using a NACS column (Bethesda Research Labs).

8. Digestion with restriction endonucleases

DNA was digested with restriction endonucleases (REN) in 1 x "AA" buffer [10 x AA buffer is 330 mM Tris-acetate, pH 7.9, 660 mM potassium acetate, 100 mM magnesium acetate, 50 mM dithiothreitol (DTT) and 1 mg/ml bovine serum albumin (nuclease free)]. Whenever possible, the concentration of DNA was kept below 1 μg/25 μl. Incubation was at 37° C. for 1-4 hrs for most restriction endonucleases except for BalI, BanI and NaeI digestions which were incubated overnight.

9. Analytical agarose gel electrophoresis of DNA

To DNA samples for gel analysis we added 0.2 volumes of loading buffer (5 x electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1 x TAC or ½ x TBE. The 1 x TAC is 40 mM Tris-base, 10 mM EDTA, adjusted to pH 7.8 with acetic acid. The ½ x TBE is 0.045M Tris-base, 0.045M boric acid, 1 mM EDTA, pH 8. The gel was run at 40-50 V for 18 hr, then removed and stained with 0.5 μg/ml ethidium bromide for 30 min. The DNA bands were visualized on a long wavelength UV transilluminator.

10. Preparative agarose gel electrophoresis

The procedures and materials are the same as for the analytical agarose gel electrophoresis. The only difference is the use of low melting point agarose, ranging in concentration from 0.5 to 2.5% (w/v) depending on the size of the DNA fragment to be purified. DNA restriction fragments were excised from the LMP agarose gels after visualization with ethidium bromide.

11. NACS purification

Gel fragments containing DNA were melted at 70° C. for 5 min and diluted approximately 5 fold with TE1 (10 mM Tris-HCl pH 7.5, 0.2M NaCl). The gel solution was applied to a NACS column (BRL). The column was washed with 5 ml of the same buffer. The bound DNA was eluted with 300 μl of either TE2 (10 mM Tris-HCl pH 7.5, 1.0M NaCl) for DNA fragments smaller than 1000 bp or TE3 (10 mM Tris-HCl pH 7.5, 2M NaCl) for larger fragments. The eluted DNA was concentrated by ethanol precipitation.

12. DNA ligation

Reactions for ligating cohesive ends contained: 1 μg DNA, 1 x AA buffer (see step 8, above) 1 mM ATP and 20 units of T4 DNA ligase (BRL) in a 20 μl final reaction volume. The ligation was allowed to proceed for 16-18 hr at 15° C. or 1-2 hr at room temperature. For blunt-ended ligations the reactions contained 1 μg DNA, 25 mM Tris-HCl pH 7.5, 5 mM $MgCl_2$, 5 mM DTT, 0.25 mM spermidine, 200 mg BSA, 1 mM hexamine cobalt chloride (HCC), 0.5 mM ATP and 400 units T4 DNA ligase (NEB) in a 20 μl reaction volume. The ligation was allowed to proceed for 30 min to 1 hr at rom temperature.

Bacterial Transformation Methods

1. Preparation of transformation-competent E. coli cells p A culture of 200 ml of sterile L broth was inoculated with a small loopful of *E. coli* cells. This was incubated with shaking at 37° C. until the $OD_{600}$ was approximately 0.5. The culture was placed on ice for 10 min and centrifuged at 6,000 xg for 10 min. The cell pellet was resuspended in 100 ml of ice-cold 0.1M $MgCl_2$, kept on ice for 30-40 min and centrifuged again. The pellet was resuspended in 2 ml of ice-cold 100 mM $CaCl_2$, transferred to a sterile test tube and incubated on ice for 24 hr. The competent cells were then aliquoted and stored at $-70°$ C.

2. Transformation of E. coli

An aliquot of frozen competent cells were thawed on ice. To 50 μl of cells 0.1 to 1 μg of DNA was added and the mixture was incubated on ice for 30 min. The tube was removed from ice and placed in a 42° C. bath for 2 min. L broth (1 ml) was added and the transformation mix incubated with shaking at the desired temperature (usually 30° C. or 37° C.) for 2 hr. Then one-tenth of the transformation was plated on L broth plates containing the appropriate antibiotic and, when necessary, XGAL and IPTG were added.

3. DNA transformation of B. subtilis

*B. subtilis* cells were grown to early stationary phase (change in Klett units of ≦5% in 15 min.). Transformation followed established procedures (Anagnostopoulos et al., 1981) (ref. 8). Cells (0.45 ml) were incubated with 1-10 μg of DNA at 37° C. for 80 min with shaking, and then plated on TBAB agar plates with an appropriate antibiotic.

4. Isolation of plasmid DNA from B. subtilis

Plasmid DNA from *B. subtilis* was obtained by a method similar to the alkaline-lysis method except that pelleted cells were resuspended in 8 ml of solution 1 (50 mM glucose, 10 mM EDTA, 25 mM Tris-HCl (pH 8.0), 10 mg/ml lysozyme) and incubated at room temperature for 30 min. Then 16 ml of solution 2 (0.2N NaOH, 1% (w/v) SDS) was added and incubated on ice for 10 min. Finally, 12 ml of 3M potassium acetate (pH 4.8) was added and incubated an additional 20 min on ice. The lysed cells were centrifuged 15 min at 15,000 rpm in a Sorval SS-34 rotor. The DNA was precipitated by adding an equal volume of isopropyl alcohol and centrifuged at 7,000 rpm. The pellet was resuspended in 5 ml of 10 mM Tris-HCl (pH 7.5), 1 mM EDTA (TE). The solution was phenol extracted once and chloroform extracted. DNA was precipitated with ethanol and resuspended in 3 ml of TE. The volume was adjusted to 5.2 ml by adding 4.2 g CsCl, 400 μl of ethidium bromide at 10 mg/ml and TE. The solution was transferred to a Beckman quick-seal polyallomer centrifuge tube and centrifuged at 45,000 rpm in a Beckman vti65 rotor for 18 hr.

Antibody Production, Protein Chemistry and Electrophoresis of Proteins

1. Preparation of antibody to artificially synthesized peptides

Synthetic peptide of sequence $(GAGABS)_8GAAGY$ was coupled to BSA using the gluteraldehyde procedure of Kagen and Glick (1979). The degree of coupling was monitored using trace amounts of radioactive iodinated synthetic peptide. Peptide conjugates at a concentration of 1 mg/ml in complete Freund's adjuvant were used to immunize rabbits at day 0. Animals were reinjected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p 328.

A peptide of 53 amino acids corresponding to the SlpIII sequence was prepared on an Applied Biosystems peptide synthesizer. The yield of this material, which has a molecular weight of 3640 was approximately 0.5 grams. The peptide was coupled to bovine serum albumin. The material was sent to Antibodies, Inc. for preparation of antibodies in rabbits. Antisera was obtained that reacted with synthetic peptides of both the SlpI and SlpIII sequences. These antisera have been useful for the detection of fusion peptides containing gly-ala sequences.

Following the procedure described above an antigen was synthesized having the formula $(V-P-G-V-G)_8$, which was coupled to keyhole limpet hemocyanin. Polyclonal antisera was then prepared as described above which bound to the ELP peptide.

2. Polyacrylamide gel electrophoresis of proteins

Approximately $10^9$ *E. coli* cells from growing cultures were pelleted by centrifugation at 10,000 xg of 5 min. The cell pellets were resuspended in 100 to 500 μl of 2 X sample buffer (100 mM Tris-HCl pH 6.8, 4% SDS, 10% B-mercaptoethanol, 60% glycerol or sucrose) and sonicated for 30 sec using a Tekmar sonic disruptor. Samples were boiled for approximately 5 min and 20 to 100 μl of the cell lysates were loaded on an SDS-polyacrylamide gel (7.5 to 16% w/v). The gels were prepared following the procedure of Laemmli (*Nature*, 227:680-685 (1970)). The proteins in the gels were stained with 2% Coomassi brilliant blue in 10% methanol, 7.5% acetic acid for 1 hr and destained in 10% methanol, 7.5% acetic acid overnight.

3. Immunoblotting of proteins in gels

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM11307) was saturated with transfer buffer and laid on the gel. Air bubbles between the filter and the gel were removed. The gel and nitrocellulose filter were placed in the transfer unit as specified by manufacturer (Bio-Rad). Transfer was allowed to proceed at 200 mA for 3-4 hr. Then the nitrocellulose filter was removed and stained with Amido-Schwartz for 3 min (0.05% Amido black, 45% deionized $H_2O$), 45% methanol, 10% acetic acid) and destained in $H_2O$. The filter was incubated for at least 10 min at room temperature in "BLOTTO" (5% w/v nonfat dry milk, 50 mM Tris-HCl pH 7.4, 0.9% w/v NaCl, 0.2% w/v sodium azide). The filter was placed in serum appropriately diluted (1:50 to 1:500) in 0.5X Blotto (2.5% nonfat dry milk, 50 mM Tris-HCl pH 7.4, 0.9% NaCl, 0.2% sodium azide) and was gently agitated for approximately 16 hr at room temperature. The filter was washed for 1 hr with 5 changes of TSA (50 mM Tris-HCl pH 7.4, 0.9% NaCl, 0.2% sodium azide). The blot was placed in 15 ml of 0.5 X BLOTTO solution containing $1 \times 10^7$ cpm of the $^{125}$I-protein A and gently agitated for 2 hr at room temperature. The filter was washed for 2 hr with a minimum of 7 changes of TSA, rinsed once with deionized $H_2O$ and air dried. The blot was covered with Saran wrap and autoradiographed.

4. Amino Acid Analysis

Amino acid composition are determined by the PTC derivitization procedure of Henrickson and Meredith (1984). Protein samples were hydrolysed with 5.7N constant boiling HCl at 108° C. for 24 hours in vacuo. After reaction with PITC, amino acid derivatives were detected at 254 nm by HPLC reverse phase chromatography using a Hewlett Packard 1090 system and a Supelco C18 column (4.6 mm × 25 cm) with a linear gradient of 0-50% acetonitile in 0.1M $NH_4OAc$ pH 6.78 as a mobile base. Henrickson, R. L. and Meredith, S. C. (1984) Amino Analysis by Reverse Phase High Performance Liquid Chromatography. *Anal. Biochem.* 137:65-74.

5. Amino Acid Sequence Analysis

The N-terminal amino acid sequence was determined by automated Edman degradation using an Applied Biosystems Model 470A gas phase protein sequenator. The PTH amino acid derivatives were analyzed by reverse phase HPLC using a Hewlett Packard 1090 system and an Altex C18 column (2 mm × 25 cm) with a complex gradient buffer system.

6. Peptide Synthesis

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, 1984). Crude peptides were desalted by chromatography over Sephadex G-50. Sarin, V. K., Kent, S. B. H., Tam, J. P. and Merrifield, R. B. (1981). *Anal. Biochem.* 237:927-936. Stewart, J. M. and Young, J. D. (1984). Solid Phase Peptide Synthesis, Pierce Chemical Company, Rockford, Ill. pp 85-89.

Synthetic DNA Methods

1. In vitro DNA synthesis

The N,N-diisopropylphosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A DNA synthesizer using a 10-fold excess of protected phosphoramidites and 1 μmole of nucleotide bound to the synthesis support column. The chemistries used for synthesis are the standard protocols recommended for use with the synthesizer and have been described (Matteucci, et al., *Journal Amer. Chem. Soc.*, 103:3185-3319 (1981)). Deprotection and cleavage of the oligomers from the solid support were performed according to standard procedures as described by McBride, et al., *Tetrahedron Letters*, 24:245-248 (1983). The repetitive yield of the synthesis as measured by the optical density of the removed protecting group as recommended by Applied Biosystems (1984) was greater than 97.5%.

The crude oligonucleotide mixture was purified by preparative gel electrophoresis as described by the Applied Biosystems protocols of Nov. 9, 1984 (User Bulletin No. 13). The acrylamide gel concentration varied from 10 to 20% depending upon the length of the oligomer. The purified oligomer was identified by UV shadowing, excised from the gel and extracted by the crush and soak procedure (Smith, *Methods in Enzymology*, 65:371-379 (1980)).

2. Sequencing of DNA

DNA sequences were determined by the following methods. Fragments containing the region of interest were cloned into the multiple cloning site of M13mp18 or M13mp19 (Maniatis et al., 1982, and Norrander et al., 1983). Single-stranded DNA was prepared and sequenced by the primer extension method (Sanger et al., 1977 and Biggin et al., 1983) using 35S-deoxyadenosine 5'-(alpha-thio)-triphosphate (New England Nuclear) as label. In some cases, reverse transcriptase (Molecular Genetics) was used to extend the primer, using the dideoxy:deoxynucleosidetri-phosphate ratios utilized by Zagursky et al. (*Gene Anal. Techn.* (1985) 2:89-94). Deoxyadenosine triphosphate labeled with either $^{32}P$ or $^{35}S$ was used in these reactions. Compression artifacts which appeared in some G-C rich sequences were overcome by eliminating deoxyguanosine triphosphate from the G reaction, and using deoxyinosine triphosphate (P-L Biochemicals) at a final concentration of 37.5 μM instead. In the other mixes, the concentration of dideoxyGTP in the G reaction was 0.5 mM. All sequences were run on 6 to 8% polyacrylamide gels containing 8M urea (Sanger et al. 1978). Primers used for sequencing were purchased from P-L Biochemicals. Storage and analysis of data utilized software from both DNAstar and International Biotechnologies, Inc.

3. In vitro mutagenesis of cloned DNA

Plasmid DNA (1 μg) containing the sequence to be mutated was digested in two separate reactions. One reaction contained either one or two restriction endonucleases which cleave at sites immediately flanking the region of interest. In the second reaction, the DNA was digested with a restriction endonuclease which cleaves only once at a site distant from the sequence to be mutated. The DNA fragments generated in the first reaction were separated by agarose gel electrophoresis and the large fragment which lacks the sequence to be mutated was excised and purified. DNA from the second reaction, the large fragment of DNA from the first reaction, and a synthetic oligodeoxynucleotide of 20-30 bases in length containing the mutant sequence were mixed in a molar ratio of 1:1:250. The mixture was denatured by heating at 100° C. for 3 min in 25 to 100 μl of 100 mM NaCl, 6.5 mM Tris-HCl pH 7.5, 8 mM MgCl$_2$, and 1 mM B-mercaptoethanol. The denatured mixture was reannealed by gradually lowering the temperature as follows: 37° C. for 30 min, 4° C. for 30 min, and 0° C. for 10 min. The reaction was supplemented with 0.5 mM deoxyribonucleotide triphosphates, 1 mM ATP, 400 units of T4 DNA ligase and 5 units of *E. coli* DNA polymerase large fragment and incubated at 15° C. for 12-16 hr. The reaction mixture was then transformed into *E. coli* and antibiotic-resistant colonies were selected.

Fermentation Conditions

The fermenter is a 15 L Chemap, 10 L working volume. The culture conditions are: temperature=30° C., pH=6.8; NaOH 2.5M is used for pH regulation. The headspace pressure is below 0.1 bar. The dissolved oxygen is regulated at 50%. The air flow varies from 0.5 L/min to 20 L/min. The agitation rate varies between 200 to 1500 rpm.

The fermentor is inoculated with a 10% (v/v) inoculum growth in medium A for 15 hours at 30° C. under agitation.

Medium B was the fermentor medium. The starting volume was 5 L.

When the glucose concentration reached 1%, a concentrated solution (5x) of medium B was added to the fermentor in order to keep the glucose concentration approximately at 1%. When the culture reached an OD$_{600}$ of 60.0, the temperature was increased to 42° C. for 10 min, then lowered to 39° C. for 2.5 hours. The cells were then harvested by centrifugation and frozen at −70° C. until processed.

TABLE 1

| Constituent | g/L |
| --- | --- |
| Medium A: LB Medium | |
| NaCl | 10 |
| tryptone | 10 |
| yeast extract | 5 |
| kanamycin | $5 \times 10^{-3}$ |
| Medium B | |
| NH$_4$Cl | 4.5 |
| KH$_2$PO$_4$ | 0.76 |
| MgSO$_4$.7H$_2$O | 0.18 |
| K$_2$SO$_4$ | 0.09 |
| CaCl$_2$ | $24 \times 10^{-3}$ |
| FeSO$_4$.7H$_2$O | $7.6 \times 10^{-3}$ |
| TE | 0.5 ml |
| casamino acids | 25 |
| yeast extract | 5 |
| glucose | 20 |
| kanamycin | $5 \times 10^{-3}$ |

EXAMPLE 2

Assembly and Expression of the SlpI Gene

1. Summary of the scheme for assembling the SlpI gene

An 18 bp DNA sequence that codes for the most frequent repeating oligopeptide in the silk fibroin protein made by *Bombyx mori* [Lucas, F. and K. M. Rudall (1986) Extracellular Fibrous Proteins: The Silks. p 475-558, in Comprehensive Biochemistry, vol. 26, part B., M. Florkin and F. H. Stotz (eds.) Elsevier, Amsterdam] was synthesized in vitro. Two single-strands were synthesized, annealed together and then the resulting double-stranded segments were multimerized head-to-tail to generate concatamers of up to and exceeding 13 repeats. The structural gene for silk I that we proceeded to work with had 13 repeats that coded for the oligopeptide gagags, where g=glycine, a=alanine and s=serine. We refer to this structural gene as the "monomer". We constructed "dimeric, trimeric, tetrameric, pentameric and hexameric" SlpI genes containing 26 (SlpI-2), 39 (SlpI-3), 52 (SlpI-4), 65 (SlpI-5) and 78 (SlpI-6) repeats. There is a short intervening sequence between each monomer unit. The assembly is pictured as follows:

using T4 polynucleotide kinase and then mixed together and allowed to anneal. This resulted in the double-stranded segments aligning spontaneously head-to-tail in long concatamers. The phosphodiester bonds between segments were formed with T4 DNA ligase. The reaction was stopped by filling in the terminal cohesive ends using the Klenow fragment of DNA polymerase I. The blunt-ended repeating DNA was then ligated to the HincII REN site in plasmid vector pUC12 (Veiera, et al., *Gene* 19:259-268 (1982)). The ligated DNA was transformed into *E. coli* HB101 and transformants were selected from their ability to grow in the presence of ampicillin. The DNA of potential clones was analyzed; for size and orientation by REN digestion and gel electrophoresis. DNA sequences were determined for isolates with large inserts that were oriented properly. The "monomer" clone selected for subsequent multimerization had 13 repeats coding for the oligopeptide agagsg, Repeating DNA sequence 5'-G G T G C G G G G C A G G A A G T
                           C G C C G C G T C C T T C A C C A-5'

"Monomer"

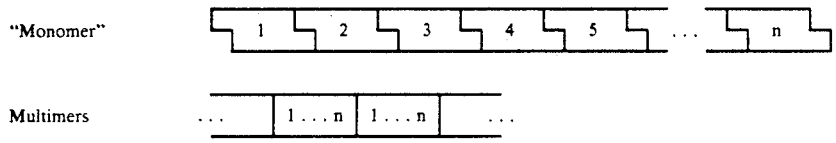

Multimers

2. Assembly of the "monomeric" SlpI structural gene

The two single-strands shown above were synthesized as previously described. The strands were separately purified by gel electrophoresis, phosphorylated and was named pSY708. The DNA sequence, deduced amino acid sequence and REN sites of the SlpI insert and flanking regions of pSY708 are shown in Table 2.

TABLE 2

```
H           P           A S
I           S           V M
N           T           A A
3           1           1 1
.           .           . .

AAGCTTGGGCTGCAGGTCACCCGGGCGGGCGCAGGAAGTGGTGCGGGCGCAGGAAGTGGT
----.----+----.----+----.----+----.----+----.----+----.----+   60
TTCGAACCCGACGTCCAGTGGGCCCGCCCGCGTCCTTCACCACGCCCGCGTCCTTCACCA k   l   g   l   q   v   t   r   a   g   a   g   s   g   a   g   a   g   s   g
----.----+----.----+----.----+----.----+----.----+----.----+----.----+

GCGGGCGCAGGAAGTGGTGCGGGCGCAGGAAGTGGTGCGGGCGCAGGAAGTGGTGCGGGC
----.----+----.----+----.----+----.----+----.----+----.----+  120
CGCCCGCGTCCTTCACCACGCCCGCGTCCTTCACCACGCCCGCGTCCTTCACCACGCCCG a   g   a   g   s   g   a   g   a   g   s   g   a   g   a   g   s   g   a   g
----.----+----.----+----.----+----.----+----.----+----.----+----.----+

GCAGGAAGTGGTGCGGGCGCAGGAAGTGGTGCGGGCGCAGGAAGTGGTGCGGGCGCAGGA
----.----+----.----+----.----+----.----+----.----+----.----+  180
CGTCCTTCACCACGCCCGCGTCCTTCACCACGCCCGCGTCCTTCACCACGCCCGCGTCCT a   g   s   g   a   g   a   g   s   g   a   g   a   g   s   g   a   g   a   g
----.----+----.----+----.----+----.----+----.----+----.----+----.----+

AGTGGTGCGGGCGCAGGAAGTGGTGCGGGCGCAGGAAGTGGTGCGGGCGCAGGAAGTGGT
----.----+----.----+----.----+----.----+----.----+----.----+  240
TCACCACGCCCGCGTCCTTCACCACGCCCGCGTCCTTCACCACGCCCGCGTCCTTCACCA s   g   a   g   a   g   s   g   a   g   a   g   s   g   a   g   a   g   s   g
----.----+----.----+----.----+----.----+----.----+----.----+----.----+

X           B           A S           E
            B           A           V M           C
            A           M           A A           R
            1           1           1 1           1
            .           .           . .           .

GCGGGCGCAGGAAGTGGGACTCTAGAGGATCCCCGGGCGAGCTCGAATTC
```

TABLE 2-continued

```
____.____+____.____+____.____+____.____+____.____+ 290
CGCCCGCGTCCTTCACCCTGAGATCTCCTAGGGGCCCGCTCGAGCTTAAG a    g   a   g   s   g   t   l   o   d   p   r   a   s   s   n   s
____.____+____.____+____.____+____.____+____.____+
```

3. Construction of the expression vector, pSY701

Plasmid pSP65 (10 μg, Boehringer Mannheim) was digested with AatII REN, phenol extracted and ethanol precipitated. The DNA was resuspended in 10 μl of H₂O. One-half of this DNA was digested with exonuclease III in the following mix: 5 μg DNA, 10 μl 10 X exonuclease III buffer (600 mM Tris-HCl pH 8.0, 6.6 mM MgCl₂, 10 mM β-mercaptoethanol) and 9 units of exonuclease III in a total volume of 200 μl. Samples of 20 μl were taken at 0, 1, 2.5, 5 and 7.5 min and diluted immediately in 100 μl of the following buffer (30 mM sodium acetate, pH 4.5, 0.25M NaCl, 1 mM ZnSO₄) containing 5 μg tRNA and 36 units of S1 nuclease. Incubation was at 30° C. for 45 min and then the reaction was terminated by the addition of 15 μl of stop buffer (0.5M Tris pH 9.0, 125 mM EDTA, 1% w/v SDS, 200 μg/ml tRNA). The samples were phenol extracted and ethanol precipitated. The resuspended DNA was digested with SmaI REN and electrophoresed through a 1% gel of low melting point agarose. The gel band corresponding to the DNA fragment carrying the β-lactamase gene, the plasmid origin and the β-galactosidase promoter was excised from the gel and melted at 65° C. One volume of H₂O was added. The DNA in each sample (timepoint) was recircularized by ligation in the presence of agarose. The reaction included 8 μl melted gel, 2 μl of ligation buffer (100 mM Tris-HCl pH 7.5, 50 mM MgCl₂, 50 mM DTT, 1 mM ATP), 10 units T4 DNA ligase and was incubated at 15° C. for 3 hr. Competent cells of JM101 were transformed with the ligated DNA and transformants were selected by growth on L broth plates containing ampicillin (40 μg/ml). Plasmid DNA was prepared from four transformants. The DNA was digested with BamHI REN, labeled with $^{32}$P-dGTP using the Klenow fragment of DNA Polymerase I, digested with Pvu I and then the smallest fragment was gel purified. The fragment from one transformant was sequenced using the Maxam and Gilbert technique. The fragments of the other three plasmids were further digested with TaqI and electrophoresed on the same gel. The sequenced plasmid had a fusion between the multiple cloning site and a position up-stream from the N-terminal ATG of β-lactamase. The size of the BamHI-TaqI fragment of two of the other plasmids indicated a fusion between the multiple cloning site and the 4th amino acid of the β-lactamase gene. The DNA and corresponding amino acid sequences of the N-terminal region of the altered β-lactamase are given below, along with a circular map of REN sites for pSY701 (see FIG. 1). The amino acid sequence of FIG. 1 is met-thr-met-ile-thr-pro-ser-leu-gly-cys-arg-ser-thr-leu-glu-asp-pro-his-phe-arg-val-ala-leu-ile-pro-phe-phe-ala-ala-phe-cys-leu-pro-val-phe-ala-his.

4. Insertion of "monomer" SlpI from pSY708 into pSY701

Plasmid pSY708 was digested with HindIII, the cohesive ends were filled in using the Klenow fragment of DNA polymerase I and then digested with BamHI. Plasmid pSY701 was digested with XbaI, filled in as above and then digested with BamHI. The DNA fragment from pSY708 and the backbone of pSY701 were then purified by electrophoresis through a low melting temperature argarose gel and purified with NACS (BRL) columns. The appropriate fragments were mixed, ligated, and then transformed into E. coli JM109. Transformed cells were selected by growth on L plates containing ampicillin (40 mg/ml), IPTG (5×10⁻⁴M) and XGAL (20 mg/ml). Transformants were analyzed for plasmid contents and one (pSY756) was selected for further study since it carried the insert on the monomer SlpI-1 sequences in the proper orientation, as determined by mapping of REN sites. Although the entire DNA sequence was not determined for pSY756, the junctions between the insert and vector were verified as correct restriction sequences for XbaI, upstream and BamHI, downstream.

5. Multimerization of the SlpI gene of pSY756

Plasmid pSY708 was digested with the REN SmaI and the DNA fragment carrying the coding sequence for the polypeptide arg(ala-gly-ala-gly-ser-gly)₁₃thr-leu-glu-asp-pro (R(AGAGSG)₁₃TLEDP) was purified as in 4 above. Plasmid pSY756 was digested with SmaI, deproteinized and then ligated with the purified DNA fragment from pSY708. Transformants of E. coli JM109 were selected on medium containing ampicillin. Clones were found to contain 2 units (dimer pSY882), 3 units (trimer pSY883), and 4 units (tetramer pSY915) of the original monomer sequence of the pSY708 clone. Similarly, pentamers and hexamers have also been constructed. All of these plasmids are genetically stable and produce the gly-ala peptide as a fusion with β-lactamase.

6. Expression of the SlpI gene fusion to the β-lactamase protein

Figure 2A:
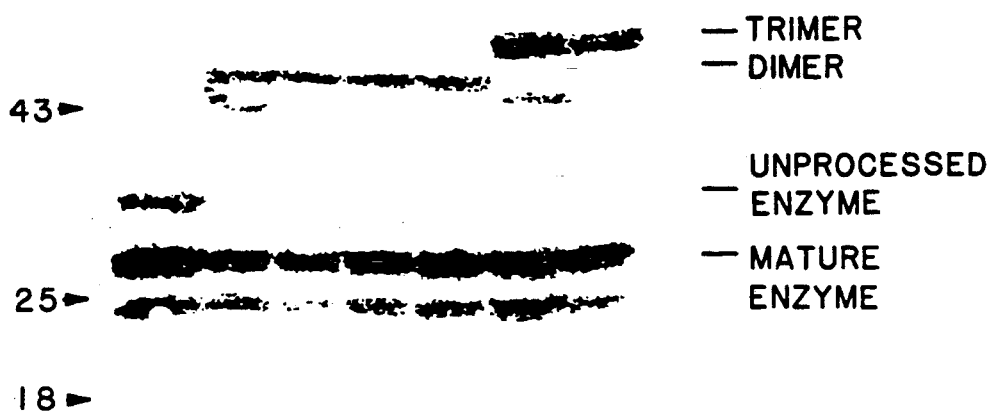
FIG. 2A–B: Immunoblots of polypeptide products using antibody to (A) beta-lactamase or to (B) gly-ala peptide.

Synthesis in E. coli cells of the SlpI peptide as a fusion protein with β-lactamase was detected by immunoblotting (Western) analysis. Anti-"Slp" antibodies were raised against a synthetic silk peptide. Fusions between β-lactamase and SlpI were also detected with antibodies raised against the E. coli β-lactamase. As shown in FIG. 2, this antibody reacts with dimers and trimers of SlpI fused to the E. coli β-lactamase. The SlpI insert proceeds the fifth amino acid of the signal sequence for this enzyme. The β-lactamase antibody (FIG. 2A) detects both the unprocessed fusion proteins as well as the processed mature enzyme which appears as the major antigenic band in this figure, at about the 28 kD position. The mobilities of all Slp-containing polypeptides are anomalously slow and the proteins are not as large as they appear on the gels.

Figure 2B:
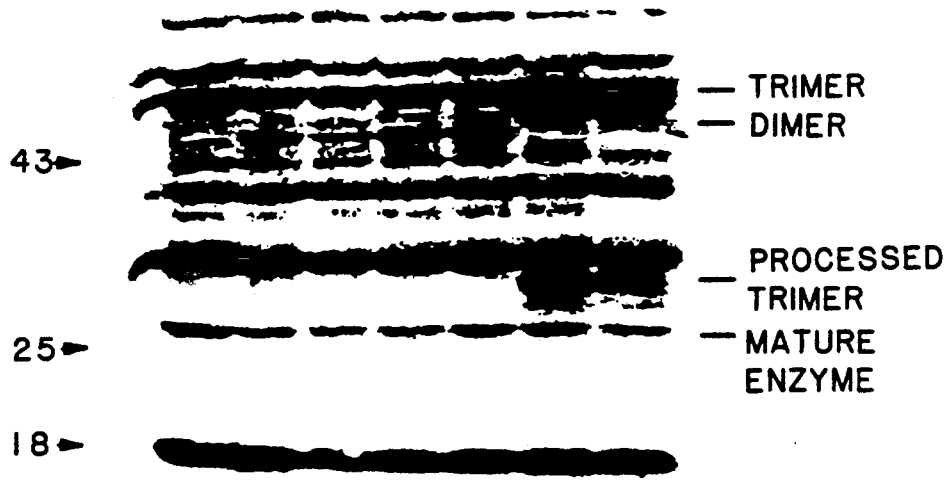

The anti-Slp antibody also is useful in detecting these fusion products. Lanes 2-5 of FIG. 2B represent 4 separate clones that contain dimer fusions of SlpI with β-lactamase, while lanes 6 and 7 are from two clones containing trimer fusions. As can be seen the antigenicity of the trimer is considerably greater than for the dimer. It is known from prior experiments that fusion proteins containing only a monomer of SlpI are not detected at all with this anti-Slp antibody. The increased antigenicity of the trimer peptide allows it to be detected as a processed fusion with the β-lactamase signal peptide. The processed form is seen at about the 33 kD position in lanes 6 and 7 of FIG. 2B. The appearance of normally processed β-lactamase mature enzyme (detected with β-lactamase antibody) as well as a peptide corresponding to the fusion between the SlpI-3 trimer and the signal peptide of β-lactamase (detected with gly-ala antibody) suggests that despite the insertion of SlpI sequences within the signal sequence, normal proteolytic processing of the enzyme occurs in *E. coli*.

7.a. Expression of the SlpI gene by fusion to T7 genes

Figure 3:
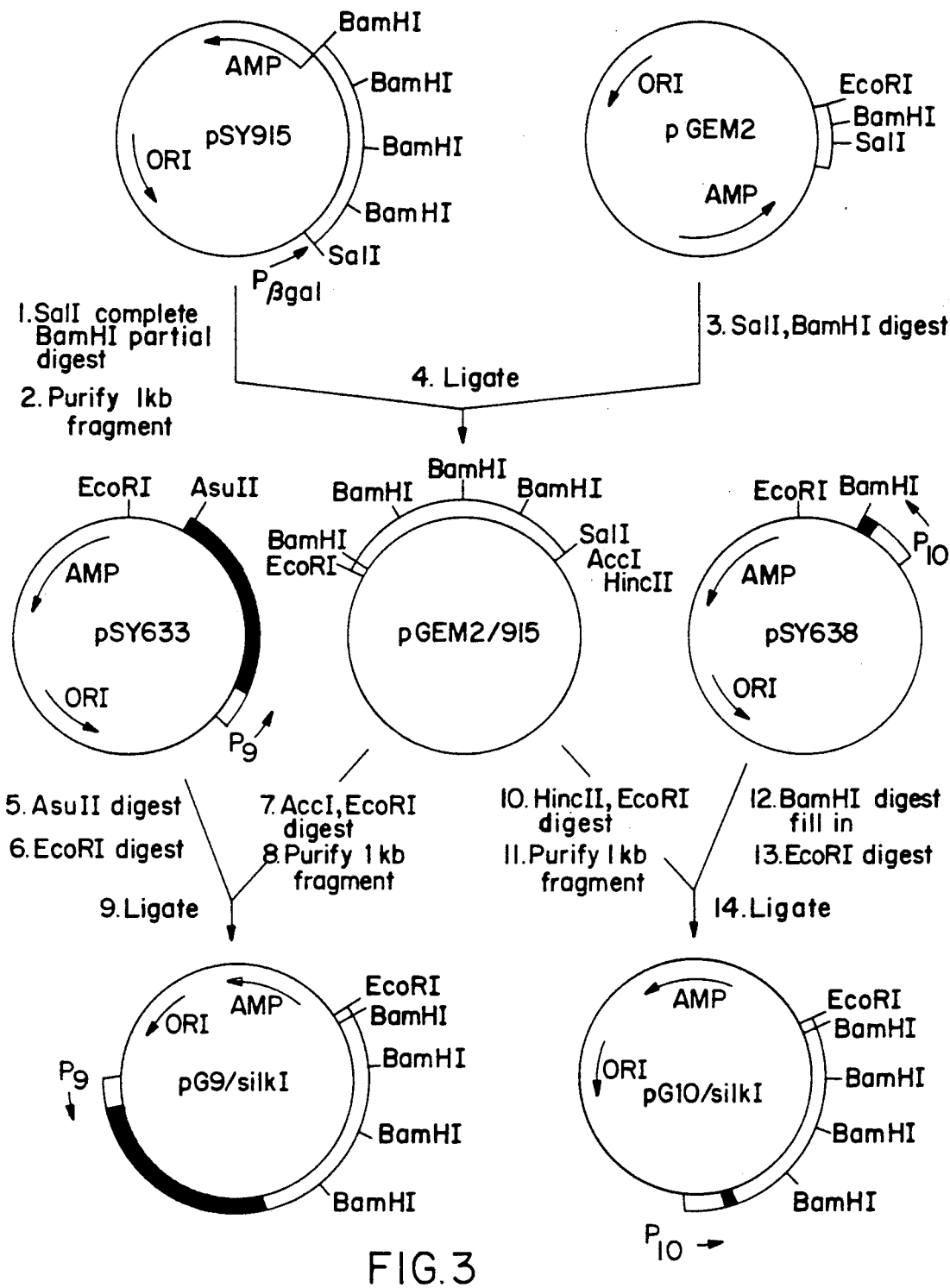
FIG. 3: Construction flowchart for plasmid pG10/SlpI.
Figure 5:
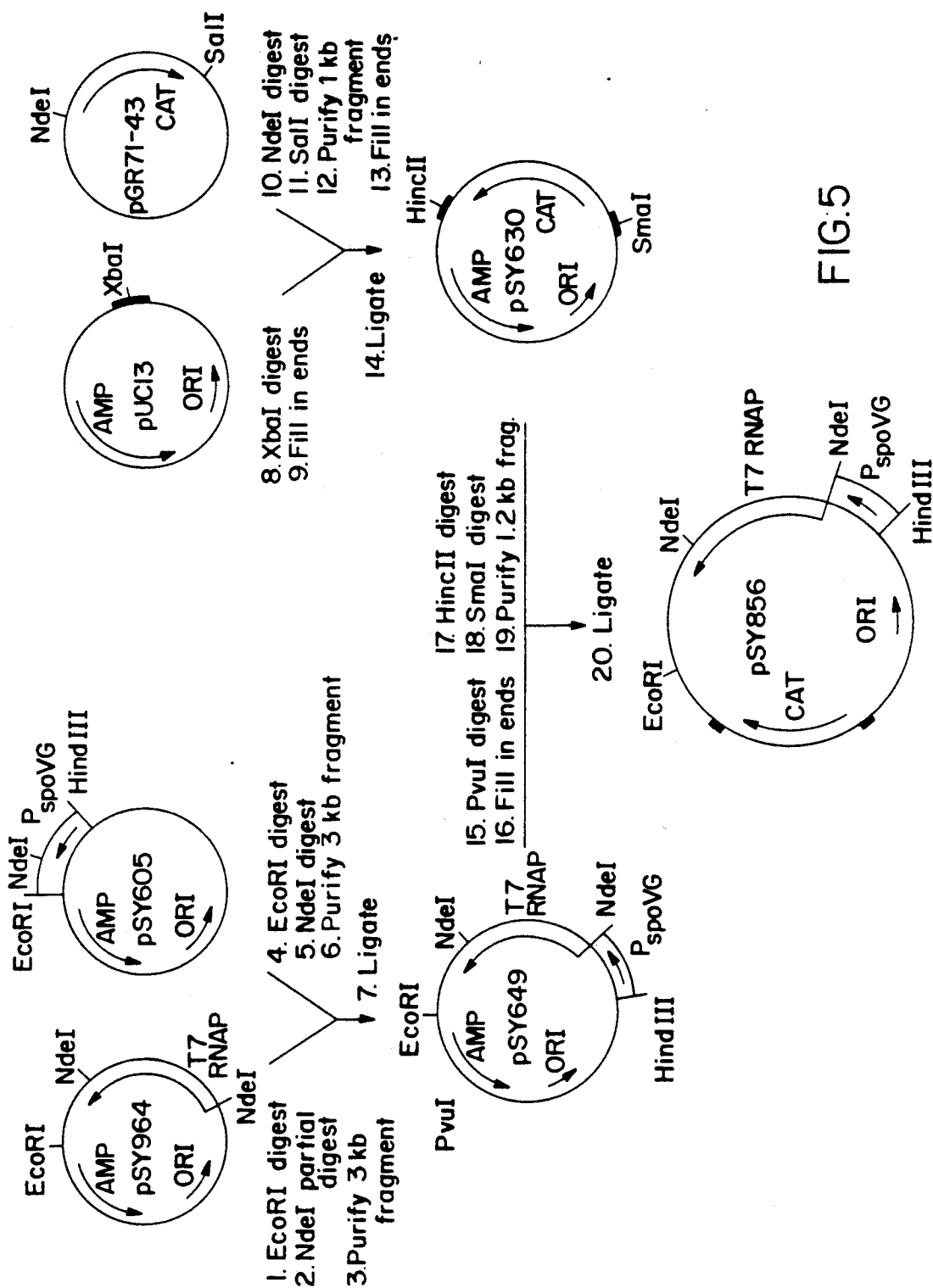
FIG. 5: Construction flowchart for plasmid pSY856.
Figure 6:
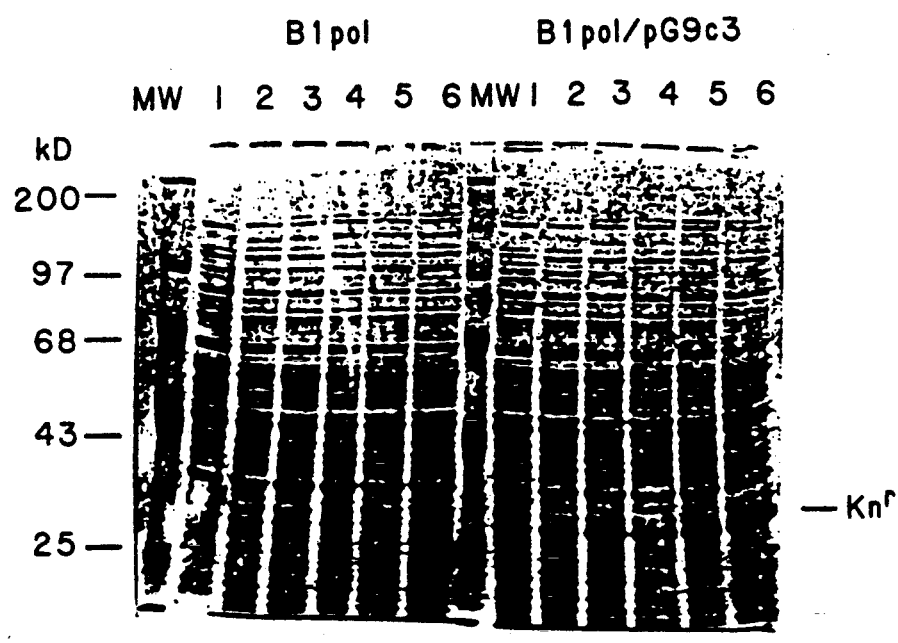
FIG. 6: Time course for accumulation of the kanamycin-resistance gene product with the T7 system.

The SlpI sequence has also been expressed as a fusion protein with both the gene 9 and gene 10 proteins from bacteriophage T7 in *E. coli*. The construction is diagramed in FIG. 3. Plasmid pSY915 (containing the SlpI-4 tetramer) was digested to completion with REN SalI and partially with BamHI. The DNA fragment containing the SlpI-4 tetramer was purified and then cloned in plasmid pSY114 (pG2 of Promega Biotech) which had been digested with RENs SalI and BamHI. From this intermediate plasmid, the tetramer insert of SlpI was removed with the RENs AccI and EcoRI. This fragment was then cloned in pSY633 (pBR322 containing the complete T7 gene 9 sequence; pAR441 of Studier et al., (1986)) which was digested with EcoRI and AsuII. In the resulting plasmid the SlpI tetramer is fused to the gene 9 translational reading frame near the C-terminus of gene 9. This plasmid was then used to transform *E. coli* strain 0-48 (strain HMS174 (λDE3) of Studier, et al., 1986) which contains the T7 RNA polymerase gene inserted into the chromosome under transcriptional control of the IPTG-inducible β-galactosidase promoter. In this configuration, expression of the SlpI-4 sequence is dependent upon production of the T7 RNA polymerase which itself is controlled by the IPTG-inducible β-galactosidase promoter. As shown in FIG. 4B and 4C, when these cells are induced with IPTG a protein product of the gene 9/SlpI-4 fusion gene is synthesized and is detected with antibody to the synthetic Slp peptide. The fusion product migrates in the gel as if it was 82 kD in size. The size expected is only 65 kD. The anomalous mobility is characteristic of the unusual amino acid composition (rich in glycine and alanine) and is seen for all Slp-containing products.

In like manner, plasmid pSY638 (pAR2113 of Studier) containing the promoter region and the first 13 amino acids of the T7 gene 10 protein, was digested with REN BamHI, filled in with the Klenow fragment of DNA polymerase and then digested with REN EcoRI. Into this linearized plasmid was cloned the AsuII-EcoRI fragment of pSY633, containing the SlpI-4 tetramer. This ligation creates an in-frame fusion of the silk tetramer following the thirteenth amino acid of T7 gene 10. The latter fusion product may be used for spinning without further processing since the N-terminal 13 amino acids are only a small part of the large SlpI protein. Although the fusion product is about 30 kD in size, it has an anomalous mobility and migrates as if it was larger, 50 kD. This is shown in FIG. 4A.

The plasmids pG9/SlpI-4 and pG10/SlpI-4 were further improved by inserting a kanamycin-resistance gene in the β-lactamase gene in the orientation opposite to the T7 expression system. Thus, any low level expression from the T7 system does not lead to elevated β-lactamase activity. Such activity eliminated the ampicillin in the medium that was added to select for maintenance of the plasmid. When the ampicillin was depleted the plasmids were lost from the culture. The kanamycin-resistance gene circumvents this problem and represents a significant improvement in the T7 expression system, especially for large scale cultures. The kanamycin-resistance gene (originally from Tn903) was isolated from a plasmid pUC4K (Veira, J. and J. Messing, 1982. *Gene*. 19:259–268) was a HincII fragment.

7.b. Fermentation and purification of SlpI-4

*E. coli* strain 0-48 carrying pSY997 was grown at 37° C., using a Chemap or a Braum fermentor, in 10 L of LB to an OD (Klett units) of 300 ($3 \times 10^9$ cells/ml). The T7 system was then induced with the addition of 3.5 mM IPTG. After 150 min the cells were concentrated 10× using a Millipore filter unit (Pellicon cassette system, 100,000 molecular weight cut off filter). The cell suspension was then frozen at $-70°$ C. until processing.

The cell suspension was melted in a water bath at 42° C. and lysed in a french press, and the lysate was spun at 125,000 xg for 1 hour at 25° C. The cleared supernatant was treated with DNAase (250 μm/ml) for 15 min at room temperature, then filtered through a 0.45 μm sterile filter. The filtrate volume was measured and incubated in ice with slow stirring. Then 231 mg of ammonium sulphate were added for each ml of filtrate over a period of 45 min. One ml of NaOH for each 10 g of ammonium sulphate was added to neutralize the pH. After 2 hours of continuous stirring the mixture was spun at 9,000 xg for 10 min. The pellet was resuspended in 1/10 of the original filtrate volume using distilled water. The centrifugation and resuspension was repeated three times. The pellet was resuspended in 1/10 of the original filtrate volume in distilled water. Samples were analyzed for protein concentration, amino acid composition and protein sequence by standard methods. This is one of several methods for obtaining the product. This method results in an SlpI-4 product that is greater than 90% pure. The amino acid composition is almost entirely gly, ala and ser, as expected, and the N-terminal amino acid sequence is that of the gene 10 leader.

8. Controlled expression of the T7 RNA polymerase gene in *Bacillus subtilis*

The coding sequence of the T7 RNA polymerase gene (T7 gene 1, T7 nucleotides 3128 to 5845) from plasmid pSY558 (pAR1151 of Studier, et al., 1986) was modified by in vitro mutagenesis of cloned DNA. We inserted the recognition sequence for the restriction endonuclease NdeI at position 3171. Using an oligodeoxynuclease NdeI at position 3171. Using an oligodeoxynucleotide which was synthesized as previously described, the T7 gene 1 sequence was changed from its natural sequence, TAAATG, to the modified sequence, CATATG.

Similarly, the upstream regulatory sequence of the *Bacillus subtilis* gene spoVG, obtained from plasmid pCB1291 (Rosenblum, et al., *J. Bacteriology*, 148:341–351 (1981)), was modified by in vitro mutagenesis at position 85 (Johnson, et al., *Nature*, 302:800–804 (1983)) such that it also includes an NdeI cleavage site. The upstream regulatory sequences of the spoVG gene were then ligated with the coding sequence of the T7 RNA polymerase gene via these novel NdeI cleavage sites. After transformation of *E. coli* HB101, the plasmid contents of individual ampicillin-resistant isolates were checked by restriction mapping. The correct construction was named pSY649.

Plasmid DNA containing the spoVG:T7 RNA polymerase fusion gene (pSY649) was further modified to include a chloramphenicol-resistance gene that functions in *B. subtilis*. First the NdeI to SalI fragment of about 1200 base pairs from plasmid pGR71-P43 (Goldfarb, et al., *Nature*, 293:309-311 (1981)) was isolated. This fragment carries the P43 promoter of *B. subtilis* and an adjacent chloramphenicol acetyltransferase gene from Tn9. After filling in all the cohesive ends using the Klenow DNA polymerase reaction, this fragment was inserted into the XbaI site within the multiple-cloning site of pUC13 (Veiera, et al., *Gene*, 19:259-268 (1982)). Ampicillin and chloramphenicol-resistant transformants were selected for further use. The correct plasmid construction was named pSY630. The SmaI to HincII endonuclease cleavage fragment from plasmid pSY630 containing the chloramphenicol acetyltransferase gene fused to the P43 promoter sequence was gel purified and blunt-end ligated to the PvuI site of plasmid pSY649 that had been treated first with T4 DNA polymerase. The resulting plasmid, pSY856, was then transformed into *B. subtilis* I168. Because plasmid pSY856 is unable to replicate autonomously in *B. subtilis*, stable transformants resistant to chloramphenicol must result from the integration of the plasmid into the *B. subtilis* chromosome (Ferrari, et al., *J. Bacteriology*, 154:1513-1515 (1983)). The integration event, facilitated by homologous recombination, most likely occurred at either the spoVG or the P43 loci of the bacterial chromosome (pSY856 contains DNA sequences homologous to the *B. subtilis* chromosome at only these two sites). The resulting strain, "BIPoL", was grown both in the presence and absence of chloramphenicol in order to determine the stability of the selectable marker. Expression of the T7 polymerase was obtained and this has no apparent effect on the growth or viability of this strain.

9.a. Expression of a plasmid-borne target gene (kanamycin-resistance) in *B. subtilis* strain BIPoL The *Staphylococcus aureus* plasmid pUB110 (Lacey, et al., *J. Med. Microbiology*, 7:285-297, 1974) which contains the gene coding for resistance to the antibiotic kanamycin was used to test the expression of the growth-regulated spoVG:T7 RNA polymerase gene of strain B1PoL. An EcoRI-BamHI fragment of phage T7 DNA (positions 21,402 to 22,858 containing the T7 gene 9 promoter sequence was purified from plasmid pAR441 (Studier, et al., 1986). This DNA fragment was ligated into pUB110 between the EcoRI and BamHI restriction endonuclease sites. The resulting plasmid, pSY952, contains the T7-specific promoter in the same orientation as the kanamycin-resistance gene. Plasmid pSY952 was transformed into *B. subtilis* I168 and BIPoL and these strains were analyzed for the level of expression of the polypeptide encoded by the plasmid-derived kanamycin-resistance gene. Approximately $10^9$ cells from growing cultures of I168, I168 containing pUB110, I168 containing pSY952, BIPoL, BIPoL containing pUB110, and BIPoL containing pSY952 were obtained at several times during the growth and sporulation cycle. The proteins in these cell samples were processed and analyzed by polyacrylamide gel electrophoresis.

Because the rate of transcription from the spoVG promoter increases as a function of cell density and reaches a maximum during early sporulation, an accelerated accumulation of the target protein is expected in the BIPoL strain containing pSY952 during growth as the culture enters sporulation. The results show that a protein of molecular weight 34 kilodaltons increased in abundance as the culture approaches and enters stationary phase. The size of the protein is in agreement with the predicted size of the kanamycin-resistance gene product (Sadaie, et al., *J. Bacteriology*, 141:1178-1182 (1980)) encoded in pSY952. This protein is not present in B1PoL or I168 containing pSY952 which lacks the spoVG-regulated T7 RNA polymerase gene or in B1PoL containing pUB110 which lacks the T7 promoter sequence. The maximum accumulated level of target protein after 24 hours of growth in B1PoL containing pSY952 was 20% of the total cellular protein as determined by densitometry.

9.b Expression of SlpI-4 in *B. subtilis*

Plasmid pG10SlpI was digested with EcoRI REN. After filling in the cohesive ends using the Klenow DNA polymerase reaction, the DNA was digested with BglII REN. Plasmid pSY662 was digested with SmaI and BamHI RENs. The two plasmids were then purified by electrophoresis through a low melting temperature agarose gel and purified with NACS (BRL) columns. The DNA fragment of pG10SlpI was ligated to the backbone of pSY662 and transformed into *E. coli* containing ampicillin (40 μg/ml). Transformants were analyzed for plasmid contents and one (pSY662/G10/SlpI-4) was selected for further study.

Competent cells of *B. subtilis* BIPoL were transformed with pSY662/G10/SlpI-4 and incubated at 37° C. with shaking for 90 min. The transformation mixture was then diluted 1:100 in fresh LB containing 10 μg/ml of tetracycline and incubated at 37° C. with shaking. Samples were taken and equal numbers of cells were lysed and loaded on gels for separation by SDS-PAGE. Immunoblot analysis was performed using anti-Slp antibodies to detect the synthesis of the gene 10/SlpI-4 fusion protein.

The expression of the SlpI-4 polypeptide in *B. subtilis* was detected by its seroreactivity with anti-Slp antibody, after transfer of the cellular proteins from the polyacrylamide gel to a nitrocellulose filter. We verified that the seroreactive protein was the product of the SlpI-4 gene by exhaustively treating the cellular proteins with CNBr. This should cleave after methionine residues, but since SlpI-4 lacks methionine it will remain intact. The CNBr treatment eliminated greater than 98% of the proteins stainable with Coomassie blue dye. And as expected for a protein lacking methionine, SlpI-4 remained intact and still reacted with anti-Slp serum.

EXAMPLE 3

Assembly and Expression of the SlpIII Gene

1. Summary of the scheme for assembling the SlpIII gene

The synthetic SlpIII gene codes for a protein similar to the SlpI gene and to the crystalline region of the silk fibroin protein made by the silkworm, *Bombyx mori*. SlpIII more closely resembles the silk fibroin molecule because it includes the amino acid tyrosine at regular intervals (about 50 residues), whereas multimers of SlpI do not. The SlpIII gene was assembled from smaller parts. First, three double-stranded sections of DNA of about 60 bp in length were chemically synthesized. Each section was cloned by insertion into bacteriophage M13 and the DNA sequence was verified. These sections were then removed from the vector and linked together in a specific order. This linkage of about 180 bp is named the SlpIII "monomer". "Monomers" were then linked in a specific order to yield dimers, trimers, tetramers, eta., of SlpIII. The multimers were then cloned either directly into plasmid expression vectors to detect the SlpIII protein or initially into an adapter plasmid. Insertion of the SlpIII DNA into the adapter allows for further gene manipulation and is further described later. The assembly scheme is pictured as follows:

Synthesis of double-stranded DNA sections

Section 1 = 5 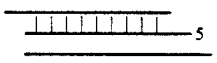 5

Synthesis of double-stranded DNA sections

Section 2 = 5 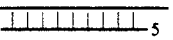 5

Section 3 = 5 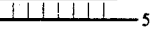 5

Assembly of "monomer" — 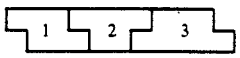

Multimerization — 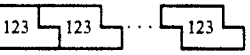

The DNA and corresponding amino acid sequences of the three sections of the SlpIII gene are shown in Table 3.

TABLE 3

```
    BanI    NaeI                                                              BanII
     :       :                                                                 :
    GGT GCC GGC AGC GGT GCA GGA GCC GGT TCT GGA GCT GGC GCG GGC TCT GGC GCA G    61bs
    CCA CGG CCG TCG CCA CGT CCT CGG CCA AGA CCT CGA CCG CGC CCG AGA CCG CGT AG   65bs
     G   A   G   S   G   A   G   A   G   S   G   A   G   A   G   S   G   A   S

BanII                                                                    PstI
     :                                                                         :
    GA TCC GGC GCA GGC GCT GGT TCT GGC GCA GGG GCA GGG TCT GGA GCT GCA          68bs
    G   CCG CGT CCG CGA CCA AGA CCG CGT CCC CGT CCC AGA CCT CGA CGT             60bs
    G   S   G   A   G   A   G   S   G   A   G   A   G   S   G   A   A

BanI                                         NaeI         PstI
                 :                                            :            :
      GGC TAT GGA GCT GGC TCA GGT GCT GGC GCA GGA AGC GGA GCG GGT GCC A         55bs
    A CGT ATA CCT CGA CCG AGT CCA CGA CCG CGT CCT TCG CCT CGC CCA CGG TTC GA    63bs
      A   G   Y   G   A   G   S   G   A   G   A   G   S   G   A   G   A
```

The double-stranded DNA sequence is shown in the 5' to 3' direction. The amino acids (g=glycine, a=alanine, s=serine, y=tyrosine) coded by the sequence are shown immediately below each section. Recognition sequences for cleavage by restriction endonucleases are shown above each section.

The above six single-strands were synthesized. After synthesis, the strands of DNA were purified and the homologous strands were annealed. About 1 μl (0.5 μg) of each strand was mixed with 2 μl of 10 X AA (description) buffer and 16 μl of sterilized deionized H$_2$O in a 1.5 ml polypropylene Eppendorf tube. The tube was placed in a boiling water bath (500 ml in a 1 liter beaker) for 10 min and then the beaker was removed from the hot plate and allowed to cool on the bench to room temperature. This required about 1-2 hr.

Each of the three double-stranded sections was cloned separately into M13mp18. Section 1 was ligated between the SmaI and BamHI restriction sites of the multiple-cloning site. Section 2 was ligated between the BamHI and PstI sites. And section 3 was inserted between the PstI and HindIII sites. The respective clones are: M13mp18.1, M13mp18.2, M13mp18.3. The DNA sequence was determined for each cloned section. One representative of each section that had the correct DNA sequence was recovered and became the material for the next step: assembly of the "monomer".

3. Assembly of the "monomer" of SlpIII

The DNA sections 2 and 3 were isolated by digestion of the M13 clones with restriction enzymes: for section 2, M13mp18.2 was digested with BamHI and Pst1; for section 3, M13mp18.3 was digested with Pst1 and HindIII. The two sections were purified and mixed together in equal molar amounts with M13mp18.1 that had been first digested with BamHI and HindIII. T$_4$ DNA ligase was added to link the homologous overlapping ends in the order 1-2-3. Due to the hybridization specificity of the cohesive ends, the three sections are efficiently linked in only this order. The DNA sequence of the cloned "monomer" in the assembly named M13mp18.1.2.3 was determined to be correct and as shown in 2 above.

4. Multimerization of the "monomer" of SlpIII

In order to prepare large amounts of the "monomer" structural gene we first subcloned the "monomer" into the plasmid vector pUC12. M13mp18.1.2.3 was digested with EcoRI and HindIII restriction enzymes. The SlpIII "monomer" was gel purified and ligated into pUC12 digested with EcoRI and HindIII. The resulting plasmid DNA was prepared, the "monomer" was released from the vector by digestion with BanI REN and the fragment was gel purified.

The create multimers, "monomer" DNA with BanI ends were linked by ligation. The nonpalindromic terminal BanI recognition sequence allows linkage only in a head-to-tail order. The extend of multimerization is monitored by gel electrophoresis and staining the DNA with ethidium bromide. Multimers of more than 20 units have been obtained by this method.

5. Cloning of the multimers of SlpIII

Figure 8:
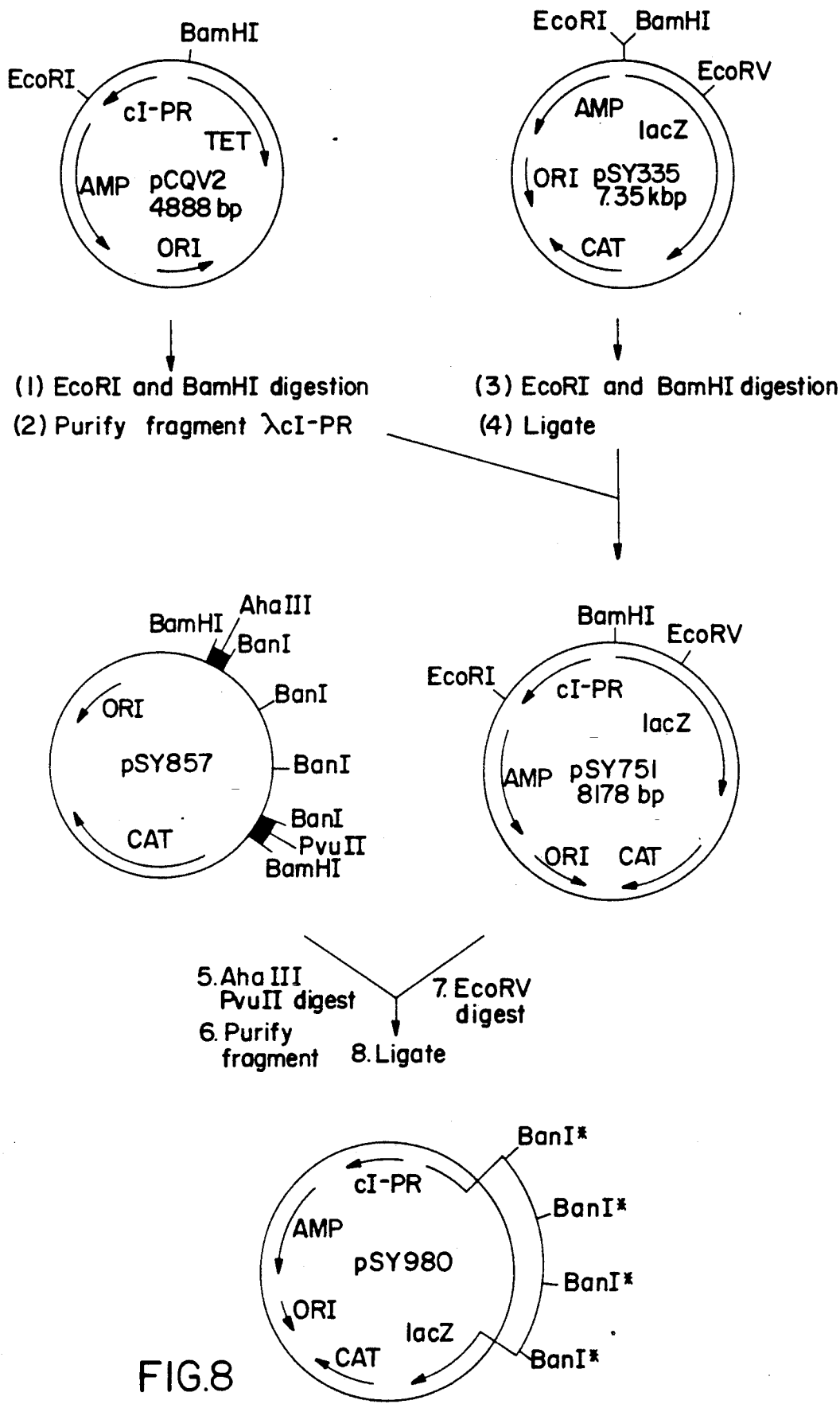
FIG. 8: Construction flowchart for plasmid pSY980.
Figure 9A:
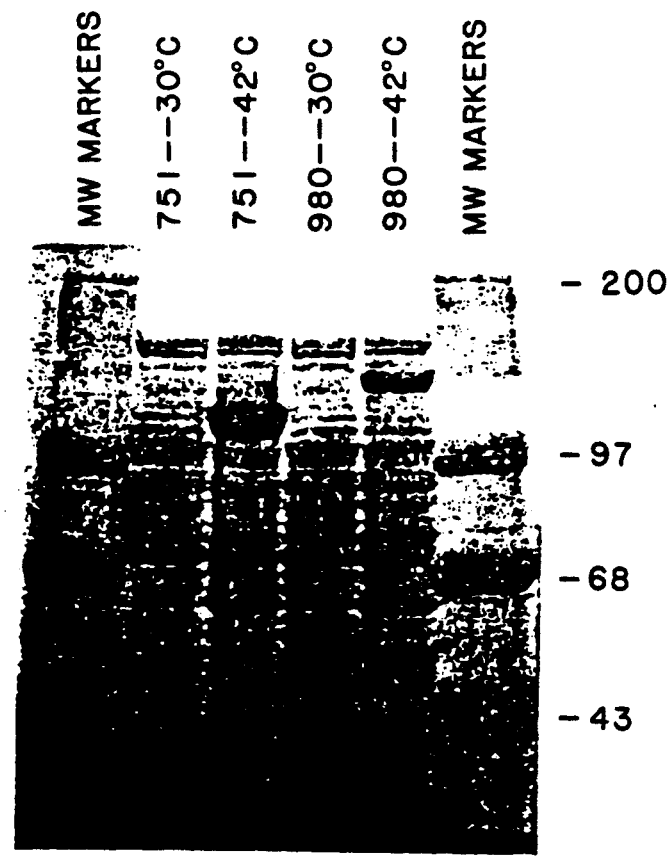
FIG. 9A–B: (A) Amido black stain or gel containing the product of beta-galactosidase/SlpIII gene fusion; (B) immunoblot of same product with anti-Slp antibody.
Figure 9B:
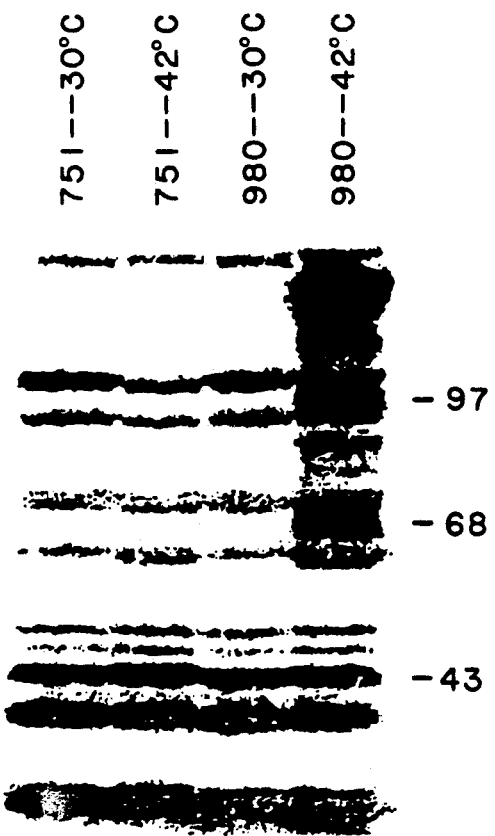
Figure 10:
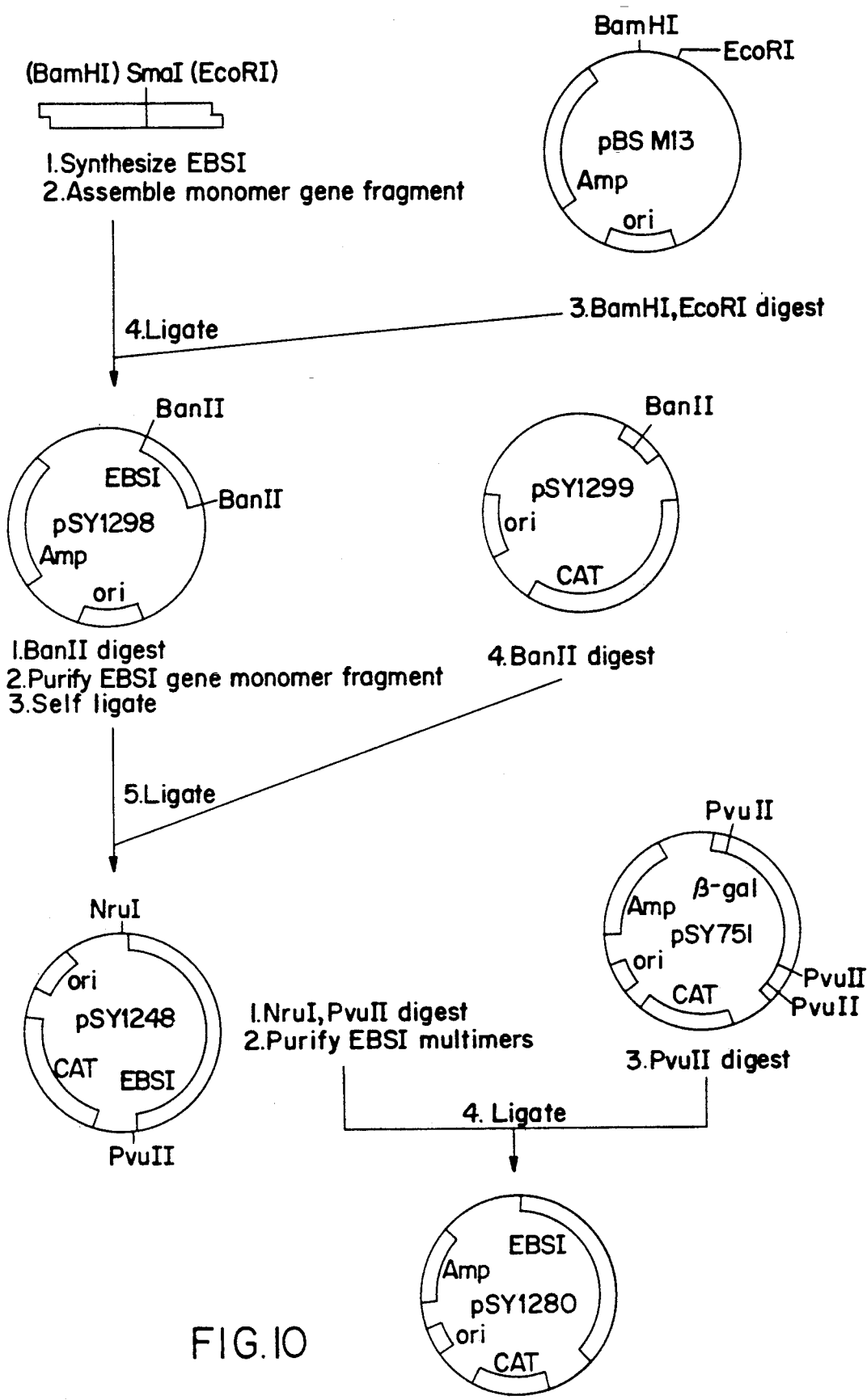
FIG. 10: Construction flowchart for plasmid pSY1280.

Plasmid pCQV2 (Queen, et al., *J. Appl. Mol. Gen.*, 2:1-10 (1983)) was digested with EcoRI and BamHI restriction endonucleases and a fragment of about 900 bp was purified. This DNA fragment contains the bacteriophage lambda cI-857 repressor gene, the closely linked rightward promoter, P$_R$, and the beginning of the cro gene. Plasmid pSY335 (described as pJF751 in Ferrari, et al., *J. Bacteriology*, 161:556-562 (1985)) was digested with EcoRI and BamHI restriction enzymes and subsequently ligated to the DNA fragment of approximately 900 bp of pCQV2. The plasmid obtained from this construction, pSY751, expresses the β-galactosidase gene at 37° C. and 42° C., but not at 30° C. (FIG. 8).

In this approach the SlpIII gene is first cloned into an "adapter" sequence in an intermediate plasmid and then subcloned to the expression systems. The adapter sequence has the following useful features: a unique central BanI REN site, three unique REN sites to either side of BanI, information coding for protein cleavage at either methionine, aspartateproline or arginine amino acids and small size. The BanI site is the point of insertion for the SlpIII multimers with BanI ends.

Figure 7:
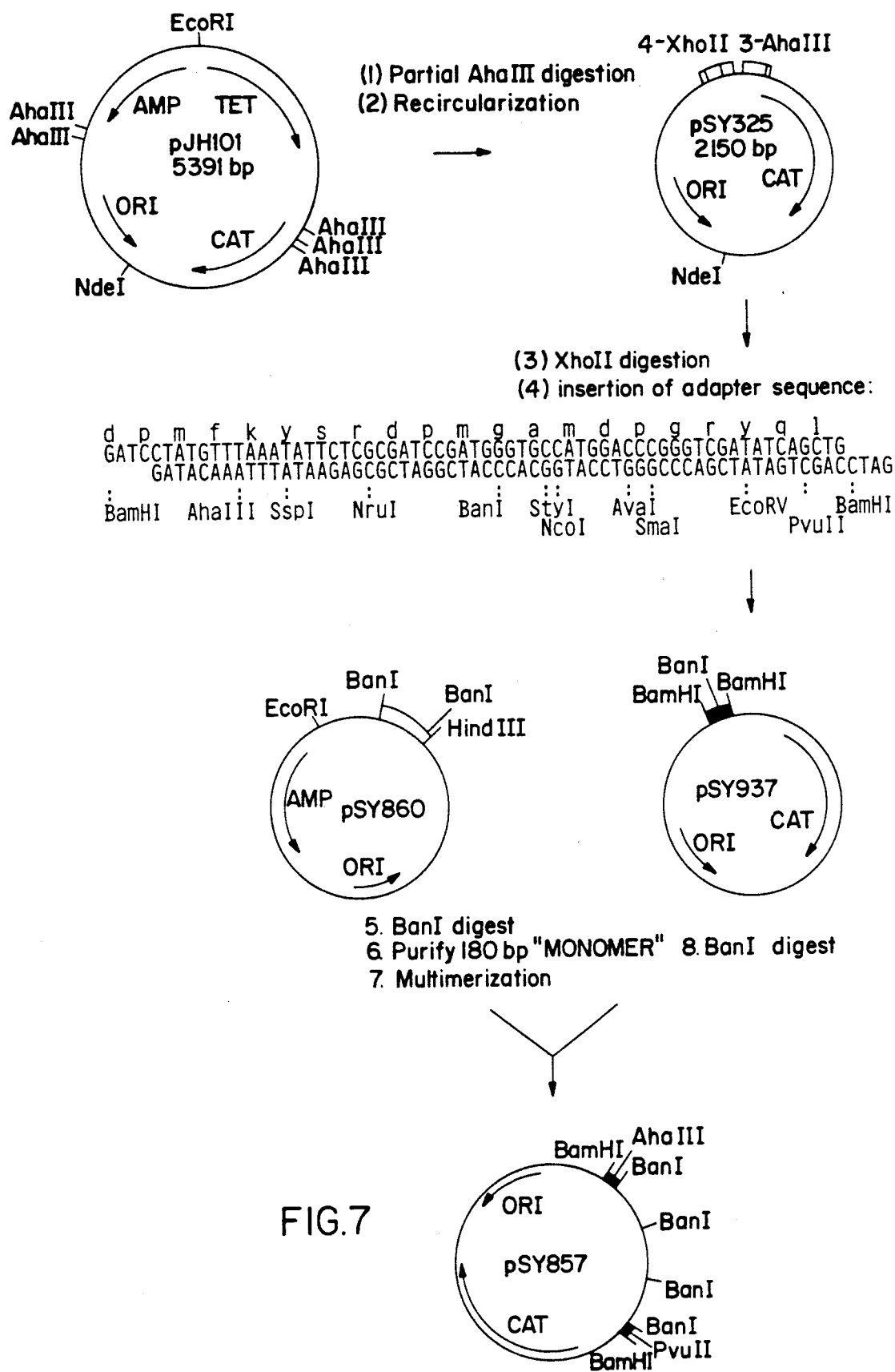
FIG. 7: Construction flowchart for plasmid pSY857.

The adapter was synthesized with the Applied Biosystems 380 A Synthesizer, cloned in M13mp18 and the DNA sequence verified. The adapter was then subcloned into a specially-constructed plasmid vector that lacked BanI REN sites. The recipient plasmid was made as follows. Plasmid pJH101 (Ferrari, et al., 1983) was partially digested with AhaIII restriction enzyme and religated. Transformants of *E. coli* HB101 were selected on medium containing chloramphenicol (12.5 mg/ml). After restriction analysis of several isolates one plasmid was chosen, pSY325 (FIG. 7). This plasmid contains only the chloramphenicol-resistance gene and the replication origin (from pBR322) of pJH101. After digestion to completion with XhoII, pSY325 was ligated with the gel-purified adapter. The result was the adapter-plasmid, pSY937, and its new REN sites were verified.

The SlpIII multimers were cloned into the BanI site of pSY937 (FIG. 7). Positive clones were identified by colony hybridization and with the lower strand of section 1 of SlpIII as the DNA probe for hybridization (probe sequence shown in Table 2). Positive clones were characterized by gel electrophoresis for the size of the inserted multimer. Finally, the SlpIII sequences were subcloned using the REN site in the flanking adapter regions to specific locations of expression plasmids.

The SlpIII protein had the following amino acid composition:

| SlpIII | 1178 AA | MW 83,000 |
|---|---|---|
| (fm) | DPVVLQRRDWENPGVTQLNRLAAHPPFASDPM | |
| | GAGS | |
| | [(GAGAGS)$_9$ GAAGY]$_{18}$ | |
| | GAGAGSGAGAGSGAGAMDPGRYQLSAGRYHYQLVWCQK | |

(fm) intends the initiation codon

SlpIII Expression Vector

Plasmid DNA pSY1086 is a pSY937 derivative containing 19 repeats of SlpIII (3.5 kb). This plasmid DNA was digested with NruI and PvuII and the fragments separated by agarose gel electrophoresis. The purified SlpIII multimer was then cloned in plasmid pSY751 digested with PvuIII REN. Several clones were analyzed and one (pSY1008) was chosen to be used in expression experiments and SlpIII purification.

The ampicillin drug resistance gene of pSY1008 was substituted with the Kanamycin marker from pSY1010 (produced by digestion of pSY633 with DraI and SspI and insertion of $Kan^R$ obtained by HincII digestion of pUC4K) and the subsequent plasmid was called pSY1186. By removing the SlpIII portion of plasmid pSY1186 with BanI, a new plasmid, pSY1262, was generated. This plasmid contains a unique BanI site which allows for the direct ligation of fragments containing BanI ends obtained by polymerization of monomers. This plasmid has been used to generate plasmids containing inserts for the following proteins: SELP1, 2, 3, and Slp4.

Production and Purification of SlpIII

Cell Culture

E. coli are cultured in the following medium:

|  | g/l |
| --- | --- |
| yeast extract | 20 |
| casamino acids | 20 |
| peptone | 20 |
| gelatin peptone | 20 |
| $KH_2PO_4$ | 2 |
| $K_2HPO_4$ | 2 |
| $Na_2HPO_4.7H_2O$ | 2 |
| glucose | 2 |
| ampicillin | 0.1 |

An overnight culture (500 ml - 1 L) which had been grown at 30° C. was used to inoculate 375 L of media contained in a 500 L fermentor. Fermentor conditions include a tachometer reading of 100 rpm, vessel back pressure of 5 psi and an air flow of 170 l/min in order to maintain dissolved $O_2$ at greater than 50%.

Glucose (1 gm/l) and ampicillin (0.05 g/l) were added to the fermentation when the culture reached an $OD_{650}$ of 1.0 and again at 2.0. When the culture reached an $OD_{650}$ of 2.0 the temperature was increased to 42° C. for 10 min and then lowered to 38° C. for 2 hours. The culture was then chilled to 10° C. and cells were harvested by centrifugation in a continuous centrifuge and frozen at $-70°$ C. until processed. Yields from two separate fermentations were 7.3 kg and 5.2 kg wet weight of cells.

It should be noted that other media can be used and, with different plasmids, various selection conditions can be imposed (i.e., substitution of kanamycin selection for ampicillin). These conditions have been used in laboratory scale fermentations (10 L volumes).

Cell Lysis

Method 1. Cells are thawed and suspended to a concentration of 1 kg wet weight/6 l in 50 mM Tris-HCl pH 7.0, 1 mM EDTA and broken by 2 passages through an APR Gaulin cell disrupter at 8000 psi. During this lysis procedure the cells are kept cold with an ice bath. The cell lysate is then centrifuged at 26,000 xg with a continuous centrifuge, such as the T2-28 rotor in a Sorvall RC5B refrigerated centrifuge operated at 4° C. Under these conditions greater than 90% of the SlPIII produced can be found in the pellet. The supernate does contain come product which can be recovered by $NH_4SO_4$ precipitation as described below. The pellet is extracted with LiBr as described below.

Method 2. Frozen cells are thawed and resuspended to a concentration of 1 kg wet weight/6 l in 50 mM Tris-HCl pH 7.0, 10 mM EDTA, and 5 mM PMSF to inhibit protease activity. Cells are stirred in this buffer at room temperature for 0.5 to 2 hours, then lysozyme is added to a concentration of 1 g/l and incubation is continued for 20 min. $\beta$-Mercaptoethanol is then added to 70 mM and the detergent NP40 is then added to a final concentration of 1% for 20 min while continuously stirring the cell suspension. Then $MgCl_2$ is added to 50 mM followed by DNAse at a concentration of 1 mg/l and incubation is continued at room temperature for 20 min. The cell lysis is then centrifuged as in method 1 at 26,000 xg in a continuous centrifuge and the supernatant is collected and passed through the continuous centrifuge a second time at 26,000 xg. The supernate resulting from this second centrifugation contains <5% of the total SlpIII, but what is there can be recovered with $NH_4SO_4$ as described below. The pellets resulting from the 1st and 2nd 26,000 xg centrifugations are combined and extracted with LiBr as described below.

Method 3. For this method, a strain of E. coli is used that contains a second plasmid which encodes the T7 phage lysozyme. This plasmid is compatible with the plasmid encoding the SlpIII gene and the drug resistance determinant. The strain is grown in the same medium and under the same conditions as in the first two methods. However, due to the production of the T7 lysozyme inside the cells, their cell wall is weakened and they can be easily lysed at the completion of the fermentation by the addition of EDTA to >100 mM and NP40 to a concentration of from 0.5 to 1.0% v/v. Lysis can also be achieved by the addition of chloroform (20 ml per liter) of fermentation broth instead of NP40. Alternatively, cells may be collected by centrifugation prior to lysis, resuspended to 1 kg wet weight/6 l in Tris-EDTA as described in the first two methods and then lysed by the addition of NP40 or chloroform. Following cell lysis by either method the lysate is centrifuged in a continuous rotor at 26,000 xg as described in the first two methods. As with those methods, LiBr extraction of the pellet and $NH_4SO_4$ precipitation of the supernate are used to recover the product.

Purification of SlpIII

The pellet obtained by centrifugation of the cell lysate at 26,000 xg as described above is extracted with an equal volume of 9M LiBr. The salt solution is added and the pellet is evenly suspended by stirring at room temperature (RT). The mixture is stirred for 1 hour at RT after an even suspension is obtained. The mixture is then centrifuged at 26,000 xg in a continuous rotor at 4° C. or at RT to generate a pellet and a supernatant fraction. The supernate is saved and the pellet is re-extracted with another equal volume of 9M LiBr as above. After mixing for 1 hour the mixture is centrifuged at 26,000 xg and the supernate from this centrifugation is combined with the supernate from the first LiBr extraction and allowed to stand at 4° C. overnight. Approximately 90% of the SlpIII contained in the cell lysate 26,000 xg pellet is extracted by LiBr using this procedure.

After the LiBr extract stands overnight at 4° C. a precipitate forms, is removed by centrifugation at 26,000 xg and is discarded. The supernatant is then placed in dialysis bags and dialyzed against several changes of $dH_2O$ for 2 days. As the LiBr is removed by dialysis the SlpIII product precipitates in the dialysis bags. The precipitate is collected by centrifugation and washed 2-3 times with dH₂O. The final washed product is centrifuged and dried by lyophilization.

For the recovery of SlpIII from the 26,000 g supernatant fractions, NH₄SO₄ precipitation is used. Solid NH₄SO₄ is slowly added to the sample which is maintained at 4° C., until 38% saturation is achieved (231 g/l). The mixture is then stirred at 4° C. for 2-3 hours. The precipitate is recovered by centrifugation in a continuous flow centrifuge and washed 4-5 times with an equal volume of distilled H₂O or with 0.5% SDS in H₂O. After each wash the precipitate is recovered by continuous centrifugation. The pellet becomes increasingly white with successive washes as contaminating protein is removed. SlpIII is recovered as a washed pellet and can be dried by lyophilization.

Trypsin Treatment Step of SlpIII

SlpIII was suspended in 50 mM Tris HCl, pH 8.0, 0.1M NaCl buffer, and was placed in a 37° C. water bath, and TPCK treated trypsin solution was mixed into the suspension. The final trypsin concentration was 0.1%. After 3 hours, the solution was centrifuged at 16,000 xg for 15 min., the pellet was washed with a half equal volume of 0.5% SDS in H₂O first, when with distilled water. After each wash the pellet was recovered by centrifugation. The final product was resuspended in water and kept at 4° C. for further analysis.

With the trypsin treatment, SlpIII was purified to 99.4% purity.

Physical Measurements of SlpIII

Physical measurements of the purified silk-like proteins have been compared with those of *Bombyx mori* silk in order to establish that the repetitive amino acid polymers produced microbiologically accurately mimic the properties of naturally occurring polymers. Physical measurements were performed to confirm the model of anti-parallel chain pleated sheet confirmation for the crystalline regions of *Bombyx mori* silk fibroin (Marsh, Corey and Pauling, *Biochem. Biophys. Acta* (1955) 16; Pauling and Corey, *Proc. Natl. Acad. Sci. U.S.A.* (1953) 39:247. Preliminary analysis of x-ray difraction patterns obtained from Slp films are consistent with those described by Fraser, MacRai, and Steward (1966) (Table 4). Circular Dichroic (CD) and Fourier transform infrared (FTIR) spectroscopic analysis of SlpIII are consistent with a high degree of extended β and β-turn conformations. Comparisons of the spectra obtained from SlpIII with that of naturally occurring silk fibroin in various solvents (Isuka and Young, *Proc. Natl. Acad. Sci. U.S.A.* (1966) 55:1175) indicate that SlpIII in solution consists of a mixture of the random and highly ordered structures ween in silk fibroins.

TABLE 4

| Material | a (A) | b (A) | c (A) |
|---|---|---|---|
| (AG)$_n$ | 9.42 | 6.95 | 8.87 |
| (AGAGSG)$_n$ | 9.39 | 6.85 | 9.05 |
| CTP fraction | 9.38 | 6.87 | 9.13 |
| Native fibroin | 9.40 | 6.97 | 9.20 |
|  | 9.44 | 6.95 | 9.30 |
| SlpIII | 9.38 | 6.94 | 8.97 |

Referenced in Fraser et al., *J. Mol. Biol.* (1966) 19:580.

EXAMPLE 4

EBSI Gene Construction

Six oligonucleotide strands were synthesized and purified as described previously.

```
        (HIII)    BanII        StuI
i.   5'AGCTGGGCTCTGGAGTAGGCCTG3' ii.  5'AATTCAGGCCTACTCCAGAGCCC3'
        (ER1)    StuI         BanII (HIII)    BanI
iii. 5'AGCTTGGTGCCAGGTGTAGGAGTTCCGGGTGTAGGCGTTCCGGGAGTTGG
     TGTACCTGGAGTGGGTGTTCCAGGCGTAGGTGTGC3'

(XmaI)
iv.  5'CCGGGCACACCTACGCCTGGAACACCCACTCCAGGTACACCAACTCCCGGA
     ACGCCTACACCCGGAACTCCTACACCTGGCACCA3'
                                    BanI (XmaI)                         AhaII
v.   5'CCGGGGTAGGAGTACCAGGGGTAGGCGTCCCTGGAGCGGGTGCTGGTAG
     CGGCGCAGGCGCGGGCTCCGGAGTAGGGGTGCCG3'
            BanII                    BanI (ERI)     BanI        BanII
vi.  5'AATTCGGCACCCCTACTCCGGAGCCCGCGCCTGCGCCGCTACCAGCACCCG
     CTCCAGGGACGCCTACCCCTGGTACTCCTACC3'
                AhaII
```

Oligonucleotide strands (iii), (iv), (v) and (vi) were annealed and ligated with the DNA of plasmid pBSm13(+) (Stratagene) which had been digested with HindIII and EcoRI. The products of this ligation reaction were transformed into *E. coli* strain JM109. Transformant colonies were selected for resistance to ampicillin. Colonies were screened for their hybridization with ³²P-labelled oligonucleotides (iii), (v). Plasmid DNA from several positively hybridizing clones was purified and sequenced. Two of the plasmids, pSY1292 and pSY1293, contained the sequence shown for oligonucleotides (iii), (v) and (iv), (vi). These sequences contained all of the nucleotides present in this synthetic oligonucleotides except one. A G:C basepair was missing at position 7 (iii). The lack of the basepair obstructed one of the BanI sites. In order to introduce a second BanII site at the 5' end of the gene fragment, oligonucleotides (i) and (ii) were annealed and ligated with plasmid pBSm13(+) which had been digested with HindIII and EcoRI. Plasmid DNA from the transformant colonies resistant to ampicillin was purified. Two plasmids, pSY1295 and pSY1296, which were digestible with StuI, a unique site contained in the oligonucleotide sequence, were sequenced. They were both shown to contain the sequence shown for oligonucleotides (i) and (ii). Plasmid DNA from pSY1292 was digested sequentially with HindIII, SI nuclease, and EcoRI. The digestion products were separated by electrophoresis in an agarose gel and the DNA fragment of approximately 150 basepairs was excised from the gel. This DNA fragment was digested with plasmid DNA pSY1296 which had been digested with StuI and EcoRI. The products of this ligation reaction were transformed into E. coli strain JM109 and were selected for resistance to ampicillin. Colonies were screened for hybridization to $^{32}$P-labelled oligonucleotide (v). The plasmid DNA from two positively hybridizing clones was purified and sequenced. These plasmids were named pSY1297 and pSY1298. They contained the following sequence:

```
(HindIII)    BanII
    AGCT GGGCT CT GGAGT AGGT GT GCCAGGT GT AGGAGT T CCGGGT GT AGGCGT T CCGGGAG           60
    T CGACCCGAGACCT CAT CCACACGGT CCACAT CCT CAAGGCCCACAT CCGCAAGGCCCT C XmaI
    T T GGT GT ACCT GGAGT GGGT GT T CCAGGCGT AGGT GT GCCCGGGGT AGGAGT ACCAGGGG         120
    AACCACAT GGACCT CACCCACAAGGT CCGCAT CCACACGGGCCCCAT CCT CAT GGT CCCC BanII
    T AGGCGT CCCT GGAGCGGGT GCT GGT AGCGGCGCAGGCGCGGGCT CCGGAGT AGGGGT GC            180
    AT CCGCAGGGACCT CGCCCACGACCAT CGCCGCGT CCGCGCCCGAGGCCT CAT CCCCACG EcoRI
    CGAATTC
    GCTTAAG
```

EBSI Multimer Gene Assembly

The BanI acceptor plasmid pSY937 was modified in order to accept BanII terminal cohesive DNA fragments. Two oligonucleotides were synthesized for this purpose.

```
        (BamHI)      DraI    SspI         NruI                    BanII
vii. 5'GATCCT AT GT T T AAAT AT T CT CGCGA ACGT T T T T GT AT GGGCT CGAT GT GT
        T ACCGT GCGCAT GGAT AT CAGCT G3'
              FspI     EcoRV    PvuII (BamHI)   PvuII  EcoRV        FspI                      BanII
viii. 5'GATCCAGCT GAT AT CCAT GCGCA CGGT AACACAT CGAGCCC AT ACAAAAA
        CGT T CGCGAG AAT AT T T AAACAT AG3'
            NruI        SspI    DraI
```

Oligonucleotides (vii) and (viii) were annealed and ligated with plasmid DNA pSY937 which was digested with BamHI. The products of this ligation were transformed into E. coli strain JM109 and colonies were selected for resistance to chloramphenicol. Transformant colonies were screened by hybridization to $^{32}$P-labelled oligonucleotide (vii). Plasmid DNA from two positively hybridizing clones, pSY1299 and pSY1300, contained the sequence shown for oligonucleotides (vii) and (viii), as determined by DNA sequencing.

Plasmid DNA pSY1298 was digested with BanII and the digestion fragments separated by agarose gel electrophoresis. The EBSI gene fragment, approximately 150 base pairs, was excised and purified by electro-elution and ethanol precipitation. Approximately 1 μg of purified fragment was self-ligated in order to produce multimers ranging in size from 450 bp to 6,000 bp. The products of the self-ligation were then ligated with plasmid DNA pSY1299 which had been digested with BanII. The products of this ligation reaction were transformed into E. coli strain HB101. Transformants were selected for resistance to chloramphenicol. Plasmid DNA from individual transformants was purified and analyzed for increased size due to EBSI multimer DNA insertions. Ten clones (pSY1240–1249) with inserts ranging in size from 1.5 Kbp to 4.4 Kbp were obtained.

Expression of EBSI Multimer Gene

One of these clones, pSY1248, which contained a 4 Kb EBSI multimer gene was recloned in the λP$_R$ expression vector, pSY751. Plasmid DNA from pSY1248 was digested with NruI and PvuII, separated by agarose gel electrophoresis, and the DNA band corresponding to the EBSI multimer gene was excised and purified by NACS purification. DNA from plasmid pSY751 was digested with PvuII and ligated with the NruI-PvuII fragment from pSY1248. The products of this ligation were transformed into E. coli HB101, and the transformants selected for resistance to ampicillin.

Two clones were isolated containing the new plasmid pSY1280. E. coli cells containing pSY1280 were grown at 30° C. to an OD$_{600}$ of 0.7 and then shifted to 42° C. for 1.5 hours. The proteins produced by these cells was analyzed by SDS-PAGE. The separated proteins were transferred to nitrocellulose paper and detected by immunoreactivity with anti-ELP rabbit serum. A strongly reactive protein band was observed with an apparent molecular weight of 120 kD.

The Ampicillin drug resistance gene of pSY1280 was substituted with the Kanamycin marker and the subsequent plasmid was called pSY1332. This plasmid was used in fermentation for the purification of EBSI. (See Methods)

pSY1332/pSY1280   EBSI Protein   1413 AA   MW 113,159

MDPVVLQRRDWENPGVTQLNRLAAHPPFASERFCMGS
[(GVGVP)$_8$ (GAGAGSGAGAGS)$_1$]$_{26}$
MCYRAHGYQLSAGRYHYQLVWCQK

Purification of EBSI Protein

*E. coli* strain HB101 containing plasmid pSY1280 was fermented in 10L volume. The cells were concentrated by filtration and further harvested by centrifugation. Pelleted cells were stored frozen at −70° C. until processed. Frozen cells were thawed on ice and suspended in 4 ml of 50 mM Tris-HCl pH 7.0, 10 mM EDTA, 5 mM PMSF per gram wet weight of cells. The cells were broken by French pressing twice at 15,000 psi and then cooled to 0° C. The crude lysate was cleared by centrifugation at 26 kxg for 20 minutes. The supernatant proteins were precipitated by addition of solid ammonium sulfate to 20% of saturation (114 g/l). The precipitate was collected by centrifugation at 10 Kxg for 10 minutes. The pellet was resuspended in 10 ml of H$_2$O and dialyzed against 10 mM Tris pH 8.0, 0.15M NaCl at 4° C. The dialyzed solution was digested with 0.1% Trypsin (Sigma) for 1.5 hours at room temperature, and reprecipitated with 20% ammonium sulfate. The precipitated protein was resuspended in H$_2$O and dialyzed against 10 mM Tris pH 7.0, 1 mM EDTA at 4° C. The protein purity of this sample was analyzed by amino acid composition and determined to be 83%.

Elastic Properties of EBSI Protein

The soluble preparation of semi-purified EBSI protein described above was incubated at 37° C. for 30 minutes and centrifuged at 10 Kxg for 10 minutes at room temperature. This treatment caused the EBSI protein to aggregate, become insoluble, and pellet into a translucent solid. The solid was resistant to mechanical disruption either by vortexing or by maceration using a glass rod. The solid could be cut with a razor blade into strips which exhibited a high degree of elasticity. They fully retained their shape after repeated extensions and relaxations. They resisted compression and no apparent irreversible deformation of structure.

EBSI Purification

EBSI sample (−70% pure) was dialyzed in 50 mM Tris HCl, 50 mM NaCl, pH 8.0 at 4° C. overnight with one change of buffer. If precipitation was observed, the sample was centrifuged at 27,000 xg for 15 min at 4° C. All remaining steps were performed at 4° C. The supernatant was applied to a DEAE-Sephacel column which had been equilibrated with 50 mM Tris HCl, 50 mM NaCl, pH 8.0. The flow through fractions which contained EBSI were collected and pooled. NaCl was added to the pooled fractions from DEAE-Sephacel column to make a final concentration of 2M NaCl in the sample. Insoluble material was removed by centrifugation at 27,000 xg for 20 min. The supernatant was then loaded onto Phenyl-Sepharose column which was equilibrated with 50 mM sodium phosphate buffer, pH 7.0, with 2M NaCl. The column was washed extensively with buffer until no eluting protein was detected by A$_{280}$. The column was then eluted stepwise with 50 mM sodium phosphate buffer, pH 7.0 and finally with water. The EBSI active fractions were pooled and stored at 4° C. for further analysis.

With the addition of these steps to the previous procedures, 100% pure EBSI was obtained.

EXAMPLE 5

ELPI Construction and Expression

Two oligonucleotide strands were synthesized and purified as described in the Methods section.

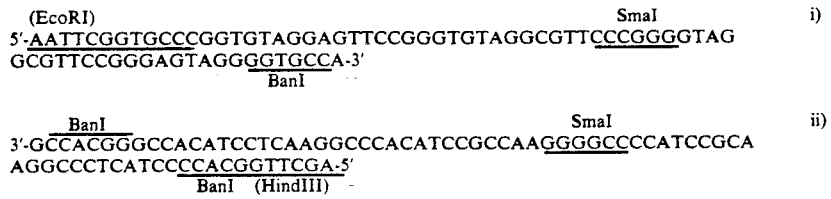

The two oligonucleotide strands were annealed and ligated with the DNA of plasmid pBS m13(+) (Stratagene) which had been digested with RENs HindIII and EcoRI.

The products of this ligation reaction were transformed into *E. coli* strain JM109. Transformant colonies were screened for their hybridization with $^{32}$P-labeled oligonucleotide (i). Plasmid DNA from positively hybridizing clones were purified and sequenced. One plasmid, pSY1287, contained the sequence shown for oligonucleotides (i) and (ii).

Plasmid DNA from pSY1287 was digested with BanI REN and the digestion fragments were separated by agarose gel electrophoresis. The ELPI gene fragment, approximately 60 bp, was excised and purified by NACS column. Approximately 1 μg of purified fragment was self-ligated in order to produce multimers ranging in size from 300 bp to 5000 bp.

The products of the self-ligation were then ligated with plasmid DNA pSY937 which had been digested with REN BanI. The product of this ligation reaction was transformed into *E. coli* strain HB101. Transformants were selected for resistance to chloramphenicol. Plasmid DNA from individual transformants was purified and analyzed for increased size due to ELPI multiple DNA insertions. Four clones (pSY1388-1391) with inserts ranging in size from 1.0 kbp to 2.5 kbp were obtained. These clones were recloned in the λP$_R$ expression vector pSY751. The clones obtained (pSY1392-1395) were used for expression of ELPI.

The ELPI protein had the following amino acid composition:

| pSY1395 | ELPI Protein | MW |
|---|---|---|
| | | 859 AA 72,555 |

MDPVVLQRRDWENPGVTQLNRLAAHPPFARNILAIRW
[(VPGVG)$_4$]$_{40}$ VPWTRVDLSAGRYHYQLVWCQK

SELP1 Gene Construction and Expression

Two oligonucleotide strands were synthesized and purified as described in the Methods section.

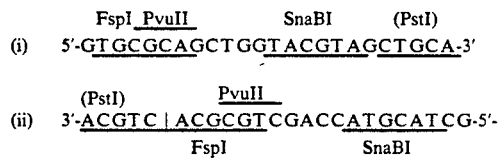

These oligonucleotide strands were annealed and ligated with plasmid pSY1304 which had been digested with PstI REN (pSY1304 differs from pSY857 by having a monomeric unit in place of the trimeric unit of pSY857). Plasmid DNA from transformant colonies resistant to chloramphenicol was purified. One plasmid, pSY1365, which was digestible with REN SnaBI, was sequenced and proven to be correct.

ELPI gene fragment purified as described (ELPI construction and expression) was treated with Mung Bean Nuclease as described by supplier (Stratagene). The DNA fragments mixture was then ligated with plasmid DNA pSY1365 which had been digested sequentially with RENs FspI, SnaBI and calf intestinal phosphatase. The products of this ligation reaction were transformed into E. coli strain HB101 and were selected for resistance to chloramphenicol. Plasmid DNA from individual transformants was purified and analyzed for the ELPI monomer DNA insertion. Two plasmids, pSY1366 A and B, were sequenced. They were both shown to contain the ELPI DNA sequence in the correct orientation.

Plasmid DNA pSY1366 was digested with REN BanI and the DNA fragment containing the SELP1 monomer was gel purified. To create multimers, 1 μg of the SELP1 DNA fragment was self-ligated. Multimers were obtained ranging in size from 500 bp to 10 kbp. The SELP1 multimers were cloned into the BanI site of pSY1262. Positive clones were characterized by gel electrophoresis for the size of the inserted multimer and used for expression and protein analysis.

gested with BanII REN and treated with calf intestinal phosphatase).

The products of the ligation mixture were transformed in E. coli strain HB101. Transformants were selected for resistance to chloramphenicol. After restriction analysis of several isolates, one plasmid was chosen, pSY1301, containing a DNA fragment corresponding to the EBSI monomer gene.

SELP2 - Multiple Gene Assembly and Expression

Plasmid DNA pSY1301 was digested with REN BanI and the DNA fragment containing the SELP2 "monomer" was gel purified. To create multimers, 1 μg of the SELP2 DNA fragment was self-ligated. Multimers were obtained greater than 12 kb in size.

The SELP2 multimers were cloned into the BanI site of pSY1262. Positive clones were characterized by gel electrophoresis for the size of the inserted multimer. The clones with inserts ranging in size from 1.5 kb to 11 kb were selected. Plasmid DNA pSY1372 containing an insert of 6 kb (18 repeats) was used for further analysis and protein purification.

SELP2 - Protein Purification

E. coli strain HB101 containing plasmid pSY1372 was fermented according to the procedure described in Methods for fermentation. The cells were harvested by centrifugation. Pelleted cells were stored frozen −70° C. until processed. Frozen cells were thawed on ice and suspended in 4ml of 50 mM Tris-HCl, pH 7.0, 10 mM EDTA, 5 mM PMSF per gram wet weight of cells. The cells were broken by passing through a Gaulin cell disrupter at 8,000 psi. The crude lysate was cleared by centrifugation at 26,000 xg for 20 min. The supernatant, which contained >75% of the SELP2 protein, was precipitated by addition of 20% ammonium sulfate (114 g/L). The precipitate was collected by centrifugation at 10,000 xg for 10 min. The pellet was resuspended in 10 ml of H$_2$O and dialyzed against 10 mM Tris pH 8.0, 0.15M NaCl at 4° C. The dialyzed material was centrifuged at 26,000 x for 15 min in order to collect the insoluble fraction of protein which contained approximately 10% of the SELP2 protein. This insoluble protein pellet was washed twice in 0.2% SDS at 50° C. for 30 min with occasional shaking. The insoluble protein was collected each time by centrifugation at 26,000 xg for 15 min. followed by a wash of 50% ethanol. The final protein pellet was resuspended in water and analyzed by Western blot analysis and amino acid composition. By Western blot the SELP2 protein appears to be homogeneous in size consistent with its large molecular weight (>150 kd). By amino acid composition the SELP2 preparation is approximately 80% pure and the observed molar ratio of amino acids (Ser:Gly:Ala:Pro:-Val:Tyr) agrees very closely with the expected composition as predicted from the SELP2 sequence present in pSY1372.

| pSY1396 | SELP1 Protein | 2025 AA | MW 148,212 |
|---|---|---|---|

MDPVVLQRRDWENPGVTQLNRLAAHPPFASDPMGAGS (GAGAGS)$_6$
[GAA(VPGVG)$_4$ VAAGY (GAGAGS)$_9$]$_{24}$
GAA(VPGVG)$_4$ VAAGY (GAGAGS)$_2$ GAGAMDPGRYQLSAGRYHYQLVWCQK

SELP2 - Monomer Construction

Plasmid DNA pSY1298 was digested with BanII REN and the EBSI gene fragment was purified as described previously. The EBSI monomer fragment was ligated into pSY1304 (pSY937 containing a monomer of SlpIII, constructed as pSY857) which had been di-

| pSY1372 | SELP2 Protein | 2055 AA | MW 152,354 |
|---|---|---|---|

MDPVVLQRRDWENPGVTQLNRLAAHPPFASDPMGAGS (GAGAGS)$_2$ (GVGVP)$_8$
[(GAGAGS)$_6$ GAAGY (GAGAGS)$_5$ (GVGVP)$_8$]$_{17}$

-continued
(GAGAGS)₆ GAAGY (GAGAGS)₂ GAGAMDPGRYQLSAGRYHYQLVWCQK

SELP3 - Construction and Expression

Plasmid DNA pSY1301 was partially digested with REN HaeII and the digestion fragments separated by agarose gel electrophoresis. The larger DNA fragments were excised and purified by NACS column. The purified fragments were self-ligated, to ligation reaction was heated at 70° C. for 15' to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1377) satisfied both requirements. Plasmid DNA pSY1377 was digested with REN BanI and the DNA fragment containing the SLP3 monomer was gel purified. To create multimers, 1 μg of the SELP3 DNA fragment was self-ligated. Multimers were obtained ranging in size from 500 bp to 10 kbp. The SELP3 multimers were cloned into the BanI site of pSY1262. Positive clones were characterized by gel electrophoresis for the size of the inserted multimer and used for expression and protein analysis.

sion to produce a wide variety of products which may mimic natural products, such as silk and other proteins and antigens. In addition, novel systems are provided for controlling the expression of the peptide under inducible conditions in a variety of hosts. In this manner, new proteinaceous products can be provided which provide for new properties or may closely mimic the properties of naturally occurring products.

BIBLIOGRAPHY

1. Maniatis, T., Fritsch, E. F. and Sambrook, J. 1982. Molecular Cloning: A Laboratory Manual. Cold Spring Harbor Laboratory, Cold Spring Harbor, N.Y.
2. Laemmli, U. K. 1970. *Nature* (London), 227:680-685.
3. Applied Biosystems User Bulletin. 1984. No. 13.
4. Matteucci, M. D. and Caruthers, M. H. 1981. *Journal Amer. Chem. Soc.*, 103:3185-3319.
5. McBride, L. J. and Caruthers, M. H. 1933. *Tetrahedron Letters*, 24:245-248.
6. Smith, 1980. *Methods in Enzymology*, 65:371-379.
7. Vieira, J. and Messing, J. 1982. *Gene*, 19:259-268.
8. Anagnostopouls, C. and Spizizen, J. 1981. *J. Bacteriol.*, 81741-746.
9. Davanloo, P., Rosenberg, A. H. Dunn, J. J. and Studier, F. W. 1984. *Proc. Natl. Acad. Sci. U.S.A.*, 81:2035-2039.
10. Rosenbluh, A., Banner, C. D. B., Losick, R. and Fitz-James, P. C. 1981. *J. Bacteriol.*, 148:341-351.
11. Sadaie, Y., Burtis, K. C. and Doi, R. 1980. *J. Bacteriol.*, 141:1178-1182.
12. Queen, C. 1983. *J. Applied Molecular Genetics*, 2:1-10.
13. Ferrari, F. A., Trach, K. and Hoch, J. A. 1985. *J. Bacteriol.*, 161:556-562.
14. Johnson, W. C., Moran, C. P. and Losick, T. R. 1983. *Nature* (London), 302:800-804.
15. Studier, W. F. and Moffat, B. A. 1986. *J. Mol. Biol.*, 189:113-130.
16. Goldfarb, D. S., Doi, R. H. and Rodriquez, R. L. 1981. *Nature* (London), 293:309-311.
17. Ferrari, F. A., Nguyen, A., Lang, D. and Hoch, J. A. 1983. *J. Bacteriol.*, 154:1513-1515.
18. Lacey, R. W. and Chopra, I. 1974. *J. Med. MIcrobiology*, 7:285-297.
19. Norrander, J., Kempe, T. and Messing, J. 1983. *Gene*, 26:101-106.
20. Sanger, F., Nicklen, S. and Coulson, A. R. 1977. *Proc. Natl. Acad. Sci. U.S.A.*, 74:5463-5467.
21. Biggin, M. D., Gibson, T. J. and Hong, G. F. 1983. *Proc. Natl. Acad. Sci. U.S.A.*, 80:3963-3965.

pSY1397     SELP3 Protein     2257 AA     MW 168,535

MDPVVLQRRDWENPGVTQLNRLAAHPPFASDPMGAGS (GAGAGS)₂
[(GVGVP)₈ (GAGAGS)₈]₂₄
(GVGVP)₈ (GAGAGS)₅ GAGAMDPGRYQLSAGRYHYQLVWCQK

SLP4 - Construction and Expression

Plasmid DNA pSY1304 (pSY857 with a single monomeric unit as distinct from the trimeric unit of pSY857) was partially digested with REN HaeII and the digestion fragments separated by agarose gel electrophoresis. The larger DNA fragments were excised and purified by NACS column. The purified fragments were self-ligated, the ligation reaction was heated at 70° C. for 15' to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1378) satisfied both requirements. Plasmid DNA pSY1378 was digested with REN BanI and the DNA fragment containing the SLP4 monomer was gel purified. To create multimers, 1 μg of SLP4 DNA was self-ligated. Multimers were obtained ranging in size from 300 bp to 6 kbp. The SLP4 multimers were cloned into the BanI site of pSY1262. Positive clones were characterized by gel electrophoresis for the size of the inserted multimer and used for expression and protein analysis.

pSY1398     SLP4 Protein     1101 AA     MW 76,231

MDPVVLQRRDWENPGVTQLNRLAAHPPFASDPMGAGS [(GAGAGS)₆]₂₇
(GAGAGS)₄ GAGAMDPGRYQLSAGRYHYQLVWCQK

As is evident from the above results, highly repetitive sequences can be prepared, cloned, and used for expres- 22. Zagursky, R. J., Baumeister, K., Lomax, N. and Berman, M. L. 1985. *Gene Anal. Techn.*, 2:89-94.
23. Sanger, F. and Coulson, A. R. 1978. *FEBS Letters*, 87:107-110.
24. Sadler, J. R., Techlenburg, M. and J. L. Betz. 1980. Plasmids containing many tandem copies of a synthetic lactose operator. *Gene* 8:279-300.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A DNA composition having a total DNA sequence of at least 900 nt encoding a peptide containing at least one oligopeptide repeating unit, which repeating unit is characterized by containing at least three different amino acids and a total of from 4 to 8 amino acids, there being at least two repeating units or multimers in said peptide and at least two identical amino acids in each repeating unit, said DNA sequence having the following formula:

$$K_k(WX_x)_i L_l$$

wherein:
K and L are each DNA sequences encoding an amino acid sequence of from about 1 to 100 amino acids, K and L being fewer than about 20 number % of the total amino acids;
k and l are 0 or 1;
W is of the formula:

$$[(A)_n(B)_p]_q$$

A is the DNA sequence encoding the repeating unit peptide GAGAGS, SGAGAG, VPGVG, or GVGVP, at least two codons coding for said identical amino acid in said repeating units being different, where there will be at least two different A's differing by at least one nucleotide;
B is a DNA sequence different from A coding for other than the oligopeptide unit coded by the A unit and having from about 3 to 45 nt, where the B units may be the same or different;
n is an integer in the range of 1 to 100;
each p is independently 0 or 1; and
q is at least 1;
X is the same as or different from W and is of the formula:

$$[(A^1)_n{}^1(B^1)_p{}^1]_q{}^1$$

wherein:
all of the symbols come within the definitions of their letter counterparts;
x is 0 or 1;
i is 1 to 100; and
the total of q, and $q^1$ is at least 2 and not greater than about 50.

2. A DNA composition having a DNA sequence according to claim 1, wherein x is 0 and A is GAGAGS, AGAGSG or SGAGAG.

3. A DNA composition having a DNA sequence according to claim 2, wherein p is 1 and B is GAA, GAAGY, VAAGY, SGAAGY or TLEDPR.

4. A DNA composition having a DNA sequence according to claim 1, wherein x is 0 and A is VPGVG or GVGVP.

5. A DNA composition having a DNA sequence according to claim 4, wherein p is 1 and B is GAA, GAAGY, VAAGY, SGAAGY or TLEDPR.

6. A DNA composition having a DNA sequence according to claim 1, wherein one of A and $A^1$ is GAGAGS, AGAGSG or SGAGAG and the other of A and $A^1$ is VPGVG or GVGVP.

7. A DNA composition having a DNA sequence according to claim 6, wherein one of B and $B^1$ is GAA, GAAGY, VAAGY, SGAAGY or TLEDPR.

* * * * *

UNITED STATES PATENT AND TRADEMARK OFFICE
CERTIFICATE OF CORRECTION

| | |
|---|---|
| PATENT NO. | : 5,243,038 C1 |
| APPLICATION NO. | : 07/114618 |
| DATED | : February 15, 2005 |
| INVENTOR(S) | : Franco A. Ferrari et al. |

It is certified that error appears in the above-identified patent and that said Letters Patent is hereby corrected as shown below:

IN THE CLAIMS

Claim 16, Col. 4, line 22, change "claim 14" to --claim 15--.

Claim 18, Col. 4, line 27, change "claim 1," to --claim 14,--.

Signed and Sealed this

Nineteenth Day of December, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 5,243,038 C1 |
| APPLICATION NO. | : 90/006028 |
| DATED | : February 15, 2005 |
| INVENTOR(S) | : Franco A. Ferrari et al. |

It is certified that error appears in the above-identified patent and that said Letters Patent is hereby corrected as shown below:

IN THE CLAIMS

Claim 16, Col. 4, line 22, change "claim 14" to --claim 15--.

Claim 18, Col. 4, line 27, change "claim 1," to --claim 14,--.

This certificate supersedes Certificate of Correction issued December 19, 2006.

Signed and Sealed this

Sixth Day of February, 2007

JON W. DUDAS
*Director of the United States Patent and Trademark Office*

(12) EX PARTE REEXAMINATION CERTIFICATE (5061st)
United States Patent
Ferrari et al.

(10) Number: US 5,243,038 C1
(45) Certificate Issued: Feb. 15, 2005

(54) CONSTRUCTION OF SYNTHETIC DNA AND ITS USE IN LARGE POLYPEPTIDE SYNTHESIS

(75) Inventors: Franco A. Ferrari, La Jolla, CA (US); Charles Richardson, San Diego, CA (US); James Chambers, San Diego, CA (US); Stuart C. Causey, Del Mar, CA (US); Thomas J. Pollock, San Diego, CA (US); Joseph Capello, San Diego, CA (US); John W. Crissman, San Diego, CA (US)

(73) Assignee: Protein Polymer Technologies, Inc., San Diego, CA (US)

Reexamination Request:
No. 90/006,028, Jun. 5, 2001

Reexamination Certificate for:
Patent No.: 5,243,038
Issued: Sep. 7, 1993
Appl. No.: 07/114,618
Filed: Oct. 29, 1987

(Under 37 CFR 1.47)

Related U.S. Application Data

(63) Continuation-in-part of application No. 06/927,258, filed on Nov. 4, 1986, now abandoned.

(51) Int. Cl.[7] .................. C12N 15/11; C12N 15/62
(52) U.S. Cl. .................. 536/23.1; 536/23.4; 435/69.1; 435/320.1; 530/353
(58) Field of Search .................. 623/11, 66, 16, 623/1; 530/328, 353; 514/15; 106/124; 427/2; 536/23.1, 23.4, 24.5; 435/69.1, 320.1

(56) References Cited

U.S. PATENT DOCUMENTS

| 4,693,718 A | 9/1987 | Urry et al. |
| 5,243,038 A | 9/1993 | Ferrari et al. |

OTHER PUBLICATIONS

Research Proposal to the Office of Naval Research, entitled "Development of Elastomeric Polypeptide Biomaterials".
Progress Report to the Molecular Biology Program of the Office of Naval Research, Contract No. N00014–86–k–0402.
Declaration of Dr. Michael T. Marron, dated Oct. 22, 1990.

*Primary Examiner*—James Ketter

(57) ABSTRACT

Methods are provided for the production of large polypeptides containing repeating sequences of amino acids utilizing biochemical techniques, specifically DNA sequences coding for the expression of the large polypeptides. Systems utilizing exogenous transcriptional and translational regions to control the production of the large polypeptides are also provided.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4 and 6 are determined to be patentable as amended.

Claims 3, 5, and 7, dependent on an amended claim, are determined to be patentable.

New claims 8–19 are added and determined to be patentable.

1. A DNA composition having a total DNA sequence of at least 900 nt encoding a peptide containing at least one oligopeptide repeating unit, which repeating unit is characterized by containing at least three different amino acids and a total of from 4 to 8 amino acids, there being at least two repeating units or multimers in said peptide and at least two identical amino acids in each repeating unit, said DNA sequence having the following formula:

$$K_k(WX_x)_i L_1$$

wherein:
K and L are each DNA sequences encoding an amino acid sequence of from about 1 to 100 amino acids, K and L being fewer than about 20 number % of the total amino acids;
k and l are 0 or 1;
W is of the formula:

$$[(A)_n(B)_p]_q$$

A is the DNA sequence encoding the repeating unit peptide GAGAGS, [VPGVG, or GVPVP] *AGAGSG, GAGSGA, AGSGAG, or* SGAGAG, at least two codons coding for said identical amino acid in said repeating units being different, where there will be at least two different A's differing by at least one nucleotide;
B is a DNA sequence different from A coding for other than the oligopeptide unit coded by the A unit and having from about 3 to 45 nt, where the B units may be the same or different;
n is an integer in the range of 1 to 100;
each p is independently 0 or 1; and
q is at least 1;
X is the same as or different from W and is of the formula:

$$[(A^1)_n^1(B^1)_p^1]_q^1$$

wherein:
all of the symbols come within the definitions of their letter counterparts;
x is 0 or 1;
i is 1 to 100; and
the total of q, and $q^1$ is at least 2 and not greater than about 50.

2. A DNA composition having a DNA sequence according to claim 1, wherein x is 0 and A is GAGAGS, AGAGSG, GAGSGA, AGSGAG, GSGAGA or SGAGAG.

4. A DNA composition having a DNA sequence according to claim 1, wherein x is [0]*1* and [A] $A^1$ is *a DNA sequence encoding the repeating unit peptide* VPGVG, *PGVGV, GVGVP, VGVPG* or [GVPVP] *GVPGV*.

6. A DNA composition having a DNA sequence according to claim 1, wherein [one of] A [and $A^1$] is GAGAGS, AGAGSG or SGAGAG and [the other of A and] $A^1$ is VPGVG or GVGVP.

*8. A DNA composition having a DNA sequence according to claim 1 wherein A is GAGAGS or SGAGAG.*

*9. A DNA composition having a total DNA sequence of at least 900 nt encoding a peptide containing at least one oligopeptide repeating unit, which repeating unit is characterized by containing at least three different amino acids, there being at least two repeating units or multimers in said peptide and at least two identical amino acids in each repeating unit, said DNA sequence having the following formula:*

$$K_k(WX_x)_i L_1$$

*wherein:*
*K and L are each DNA encoding an amino acid sequence of from about 1 to 100 amino acids, K and L being fewer than about 20 number % of the total amino acids;*
*k and l are 0 or 1;*
*W is of the formula:*

$$[(A)_n(B)_p]_q$$

*A is the DNA sequence encoding the repeating unit peptide GAGAGS, AGAGSG, GAGSGA, AGSGAG, GSGAGA, SGAGAG, VPGVG, PGVGV, GVGVP, VGVPG or GVPGV, at least two condons coding for said identical amino acid in said repeating units being different, where there will be at least two different A's differing by at least one nucleotide;*
*B is a DNA sequence different from A coding for other than the oligopeptide unit coded by the A unit and having from about 3 to 45 nt, where the B units may be the same or different;*
*n is an integer in the range of 1 to 100;*
*wherein:*
*each p is independently 0 or 1; and*
*q is at least 1;*
*X is different from W and is of the formula:*

$$[(A^1)_n^1(B^1)_p^1]_q^1$$

*wherein:*
*all of the symbols come with the definitions of their letter counterparts;*
*x is 1;*
*i is 1 to 100; and* the total of q, and $q^1$ is at least 2 and not greater than about 50.

10. A DNA composition having a DNA sequence according to claim 9, wherein p is 1 and B is the DNA sequence encoding the peptide GAA, GAAGY, VAAGY, SGAAGY or TLEDPR.

11. A DNA composition having a DNA sequence according to claim 9, wherein A is GAGAGS, AGAGSG, GAGSGA, AGSGAG, GSGAGA or SGAGAG and $A^1$ is VPGVG, PGVGV, GVGVP, VGVPG or GVPGV.

12. A DNA composition having a DNA sequence according to claim 9, wherein A is the DNA sequence encoding the repeating unit peptide GAGAGS or SGAGAG and wherein $A^1$ is the DNA sequence encoding the repeating unit peptide VPGVG.

13. A DNA composition having a DNA sequence according to claim 11, wherein one of B and $B^1$ is the DNA sequence encoding the peptide GAA, GAAGY, VAAGY, SGAAGY or TLEDPR.

14. A DNA encoding a peptide comprising an oligopeptide repeating unit, which repeating unit is characterized by containing at least three different amino acids, there being at least two repeating units in said peptide and at least two identical amino acids in each repeating unit and wherein said units are optionally joined by an amino acid bridge of from about 1 to 15 amino acids, said DNA sequence having the following formula:

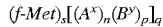

wherein:

A is a DNA sequence encoding for said oligopeptide repeating unit GAGAGS, AGAGSG, GAGSGA, AGSGAG, GSGAGA, SGAGAG, VPGVG, PGVGV, GVGVP, VGVPG or GVPGV, where A will contain at least two condons coding for said identical amino acids in said repeating unit being different;

x intends there will be at least two different A's differing by at last one nucleotide;

B is a DNA sequence different from A coding for other than the oligopeptide unit coded by the A unit and having from about 3 to 45 nt;

y intends that the B units may be the same of different;

n is an integer in the range of 1 to 100;

s is 0 or 1;

each p is independently 0 or 1; and q is at least 1 and is selected so as to provide a DNA sequence of at least 900 nt and less than 10,000 nt.

15. A DNA sequence according to claim 14, wherein said $(A)_1$ codes for GAGAGS, AGAGSG, GAGSGA, AGSGAG, GSGAGA or SGAGAG.

16. A DNA sequence according to claim 14 further comprising $(A)_2$ which encodes VPGVG, PGVGV, VGVGVP, VGVPG or GVPGV.

17. A DNA sequence according to claim 14 wherein A codes for SGAGAG.

18. A DNA sequence according to claim 1, wherein said A codes for VPGVG, PGVGV, VGVGVP, VGVPG or GVPGV.

19. A DNA sequence according to claim 14 wherein said A codes for VPGVG.

* * * * *